United States Patent [19]
Chance

[11] Patent Number: 5,807,263
[45] Date of Patent: Sep. 15, 1998

[54] IMAGING OF BIOLOGICAL TISSUE USING PHOTON MIGRATION WITH HIGH DIRECTIONALITY TECHNIQUES

[75] Inventor: Britton Chance, Marathon, Fla.

[73] Assignee: Non-Invasivie Technology, Inc., Philadelphia, Pa.

[21] Appl. No.: 356,162

[22] PCT Filed: Jun. 17, 1993

[86] PCT No.: PCT/US93/05868

§ 371 Date: Dec. 16, 1994

§ 102(e) Date: Dec. 16, 1994

[87] PCT Pub. No.: WO93/25145

PCT Pub. Date: Dec. 23, 1993

[51] Int. Cl.$^6$ ........................................ A61B 5/00
[52] U.S. Cl. .......................... 600/476; 600/473; 600/407; 600/410
[58] Field of Search ............................ 128/653.1, 653.2, 128/664, 665

[56] References Cited

U.S. PATENT DOCUMENTS

| | | | |
|---|---|---|---|
| 4,515,165 | 5/1985 | Carroll | 128/664 |
| 4,807,637 | 2/1989 | Bjorkholm | 128/665 X |
| 4,836,207 | 6/1989 | Bursell et al. | 128/665 X |
| 4,908,762 | 3/1990 | Suzuki et al. | 128/633 X |
| 4,972,331 | 11/1990 | Chance | 128/633 X |
| 5,062,431 | 11/1991 | Potter | 128/665 |
| 5,090,415 | 2/1992 | Yamashita et al. | 128/665 |
| 5,158,090 | 10/1992 | Waldman et al. | 128/664 |
| 5,174,298 | 12/1992 | Dolfi et al. | 128/665 |
| 5,203,339 | 4/1993 | Knüttel et al. | 128/665 |
| 5,213,105 | 5/1993 | Gratton et al. | 128/664 |
| 5,309,907 | 5/1994 | Fang et al. | 128/664 X |
| 5,309,912 | 5/1994 | Knüttel | 128/653 |
| 5,416,582 | 5/1995 | Knutson et al. | 356/349 |

OTHER PUBLICATIONS

Arridge et al., "Reconstruction Methods for Infra-red Absorption Imaging", SPIE, vol. 1431:204, 1991.
Barlow et al., "Breast Biopsy Analysis by Spectroscopic Imaging", Plenum Press, New York, p. 111, 1989.
Britton Chance, "The Future of Time Resolved Spectroscopy and Imaging", Aug. 5–10, 1990 Japan.
Cui et al., "Experimental Study of Migration Depth for the Photons Measured At Sample Surface", SPIE 1431:180, 1991.
Fishkin et al., "Diffusion of Intensity Modulated Near–Infrared Light in Turbin Media", SPIE 1431:122, 1991.
Gratton et al., "The Possibility of a Near Infrared Optical Imaging System Using Frequency Domain Methods in Mind Brain Imaging Program", Aug. 5–10, 1990 Japan.

(List continued on next page.)

*Primary Examiner*—Jennifer Bahr
*Assistant Examiner*—Stephen D. Huang
*Attorney, Agent, or Firm*—Fish & Richardson P.C.

[57] ABSTRACT

A method and system for examination of a subject positioned between input and detection ports of the spectroscopic system applied to the subject. The systems shown include at lease one light source for introducing at one or multiple input ports, electromagnetic non-ionizing radiation of a known time-varying pattern of photon density of a wavelength selected to be scattered and absorbed while migrating in the subject, radiation pattern control means for achieving a directional pattern of emitted resulting radiation that possesses substantial gradient of photon density, at least one detector for detecting the radiation that has migrated in the subject at one or multiple detection ports. The systems also include processing means for processing the detected radiation and creating sets of data, and evaluation means for examining the subject using the data sets. The emitted directional radiation pattern utilizes its gradient of photon density to detect a hidden object while scanning across the examined subject. The wavelength of the radiation can be selected to be sensitive to endogenous or exogenous pigments, or to cause fluorescent emission from a fluorescent constituent of interest in the subject. The operation of the systems is computer controlled.

74 Claims, 28 Drawing Sheets

OTHER PUBLICATIONS

Grunbaum et al., "Diffuse Tomography", SPIE 1431:232, 1991.

Oda et al., "Non–Invasive Hemoglobin Oxygenation Monitor and Computerized Tomography of NIR Spectrometry", SPIE 1431:284, 1991.

Sevick et al., Analysis of Absorption, Scattering and Hemoglobin Saturation Using Phase Modulation Spectroscopy, SPIE 1431:264, 1991.

Sevick et al., "Photon Migration in a Model of the Head Measured Using Time–and–Frequency–Domain Techniques Potentials of Spectroscopy and Imaging", SPIE 1431:84, 1991.

Sevick et al., "Quantitation of Time— and Frequency–Resolved Optical Spectra for the Determination of Tissue Oxygenation", Analytical Biochemistry 195:330–151, 1991.

Singer et al., "Image Reconstruction of the Interior of Bodies that Diffuse Radiation", Science 228:990, 1990.

Yamashita et al., "The Neonate Brain (NIR) and Breast Imaging Using Transillumination Photon Migration in Tissues", Plenum Press, New York, p. 55, 1989.

Becton Dickinson, "Cardio–Green (CG) HW&D Brand of Sterile Indocyanine Green, USP" Product Insert, Revised: Apr. 1981.

$$I_n e^{jw(t-t_n)} \qquad \alpha = \frac{2\pi}{\lambda} d \sin\theta_0$$

$$t_n = n \frac{d}{c} \sin\theta_0 \qquad n = 0,1,2...$$

ANTIPHASE MULTIELEMENT TRANSMITTER-RECEIVER ARRAYS

ARRANGEMENT OF PHASES FOR SCAN

|  | 1 | 2 | 3 | 4 | 5 |
|---|---|---|---|---|---|
| TRANSMITTER ARRAY 1 | −│+ | + | + | + | + |
| 2 | − | −│+ | + | + | + |
| 3 | − | − | −│+ | + | + |
| 4 | − | − | − | −│+ | + |
| 5 | − | − | − | − | −│+ |

RECEIVER ARRAY POSITION t=0

IMAGING OF BIOLOGICAL TISSUE USING PHOTON MIGRATION WITH HIGH DIRECTIONALITY TECHNIQUES

BACKGROUND OF THE INVENTION

This invention relates to examination and imaging of biological tissue using visible or infra-red radiation.

Traditionally, potentially harmful ionizing radiation (for example, X-ray or γ-ray) has been used to image biological tissue. This radiation propagates in the tissue on straight, ballistic tracks, i.e., scattering of the radiation is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer which reconstructs the X-ray absorption of the tissue at a multiplicity of points located in one cross-sectional plane.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing; thus, it potentially causes fewer side effects. However, with lower energy radiation, such as visible or infra-red radiation, the radiation is strongly scattered and absorbed in biological tissue, and the migration path cannot be approximated by a straight line, making inapplicable certain aspects of cross-sectional imaging techniques.

Recently, certain approaches to NIR imaging have been suggested. One approach undertaken by Oda et al. in "Non-Invasive Hemoglobin Oxygenation Monitor and Computerized Tomography of NIR Spectrometry," SPIE Vol. 1431, p. 284, 1991, utilizes NIR radiation in an analogous way to the use of X-ray radiation in an X-ray CT. In this device, the X-ray source is replaced by three laser diodes emitting light in the NIR range. The NIR-CT uses a set of photomultipliers to detect the light of the three laser diodes transmitted through the imaged tissue. The detected data are manipulated by a computer of the original X-ray CT scanner system in the same way as the detected X-ray data would be.

Different approaches were suggested by S. R. Arriadge et al. in "Reconstruction Methods for Infra-red Absorption Imaging," SPIE Vol. 1431, p. 204, 1991; F. A. Grünbaum et al. in "Diffuse Tomography," SPIE Vol. 1431, p. 232, 1991; B. Chance et al., SPIE Vol. 1431 (1991), p. 84, p. 180, and p. 264; and others who recognized the scattering aspect of the non-ionizing radiation and its importance in imaging. None of those techniques have fully satisfied all situations.

In summary, there continues to be a need for an improved imaging system which utilizes visible or IR radiation of wavelengths sensitive to endogenous or exogenous pigments.

SUMMARY OF THE INVENTION

The invention relates to systems and methods for spectroscopic examination of a subject positioned between input and detection ports of the spectroscopic system applied to the subject.

According to one aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; and radiation pattern control means adapted to achieve a selected time relationship of the introduced patterns to form resulting radiation that possesses a substantial gradient in photon density as a result of the interaction of the introduced patterns emanating from the input ports, the radiation being scattered and absorbed in migration paths in the subject. The gradient in photon density may be achieved by encoding the introduced radiation patterns with a selected difference in their relative amplitude, relative phase, relative frequency or relative time. The system also includes a detector adapted to detect over time, at a detection port placed at a selected location on the subject, the radiation that has migrated in the subject; processing means adapted to process signals of the detected radiation in relation to the introduced radiation to create processed data indicative of the influence of the subject upon the gradient of photon density; and evaluation means adapted to examine the subject by correlating the processed data with the locations of the input and output ports.

Preferred embodiments of this aspect of the invention include displacement means adapted to move synchronously all the optical input ports or move the detection ports to another location on a predetermined geometric pattern; at this location the examination of the subject is performed.

According to another aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; radiation pattern control means adapted to achieve a selected time relationship of the introduced patterns to form resulting radiation that possesses a substantial gradient in photon density as a result of the interaction of the introduced patterns emanating from the input ports, the radiation being scattered and absorbed in migration paths in the subject. The system also includes a detector adapted to detect over time, at a detection port placed at a selected location on the subject, the radiation that has migrated in the subject; displacement means adapted to move the detection port to various locations on a predetermined geometric pattern, the various locations being used to detect over time radiation that has migrated in the subject; processing means adapted to process signals of the detected radiation in relation to the introduced radiation to create processed data indicative of the influence of the subject upon the gradient of photon density; and evaluation means adapted to examine the subject by correlating the processed data with the locations of the input and output ports.

According to another aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; radiation pattern control means adapted to achieve a selected time relationship of the introduced patterns to form resulting radiation that possesses a substantial gradient in photon density as a result of the interaction of the introduced patterns emanating from the input ports, the radiation being scattered and absorbed in migration paths in the subject. The system also includes at least one detector adapted to detect over time, at multiple detection ports placed at selected locations on the subject, the radiation that has migrated in the subject; processing means adapted to process signals of the detected radiation in relation to the introduced radiation to create processed data indicative of the influence of the subject upon the gradient of photon density, and evaluation means adapted to examine the subject by correlating the processed data with the locations of the input and output ports.

Preferred embodiments of this aspect of the invention include displacement means adapted to move at least one of the detection ports to another location on a predetermined geometric pattern, the other location being used to perform the examination of the subject.

Preferred embodiments of this aspect of the invention include rotation means adapted to rotate synchronously the optical input ports while introducing the resulting radiation along a predetermined geometric pattern, the input port rotation being used to perform the examination of a region of the subject.

Preferred embodiments of the above described aspects of the invention are also used to locate a fluorescent constituent of interest in the subject; the wavelength of the introduced radiation is selected to be absorbed in the fluorescent constituent, the detected radiation is emitted from the fluorescent constituent and processed to determine location of the fluorescent constituent.

According to another aspect of the invention, a spectroscopic system includes a light source adapted to introduce, at an input port, electromagnetic non-ionizing radiation of a known time-varying pattern of photon density and of a wavelength selected to be scattered and absorbed while migrating in the subject, the input port being placed at a selected location on the subject to probe a selected quality of the subject; detectors adapted to detect over time, at multiple detection ports placed at selected locations on the subject, the radiation that has migrated in the subject; the time relationship of the detection over time, at the detection ports, being selected to observe a gradient in photon density formed as a result of the interaction of the introduced radiation with the subject. The system also includes processing means adapted to process signals of the detected radiation in relation to the introduced radiation to create processed data indicative of the influence of the subject upon the gradient of photon density, and evaluation means adapted to examine the subject by correlating the processed data with the locations of the input and output ports.

Preferred embodiments of this aspect of the invention include displacement means adapted to move at least one of the detection ports to another location on a predetermined geometric pattern, the other location being used to perform the examination of the subject.

According to another aspect of the invention, a spectroscopic system includes a light source adapted to introduce, at an input port, electromagnetic non-ionizing radiation of a known time-varying pattern of photon density and of a wavelength selected to be scattered and absorbed by a fluorescent constituent while migrating in the subject, the input port being placed at a selected location on the subject to locate the fluorescent constituent of the subject; detectors adapted to detect over time, at multiple detection ports placed at selected locations on the subject, fluorescent radiation that has migrated in the subject. The system also includes processing means adapted to process signals of the detected radiation in relation to the introduced radiation to create processed data indicative of location of the fluorescent constituent of the subject, and evaluation means adapted to examine the subject by correlating the processed data with the locations of the input and output ports.

Preferred embodiments of this aspect of the invention include displacement means adapted to move at least one of the detection ports to another location on a predetermined geometric pattern, the other location being used to locate the fluorescent constituent of the subject.

Preferred embodiments of the above-described aspects of the invention use one or more of the following features:

The time-varying pattern comprises radiation of a selected wavelength intensity modulated at a selected frequency. The radiation pattern control means are further adapted to control a selected phase relationship between the modulated radiation patterns introduced from each of the input ports having to produce in at least one direction a steep phase change and a sharp minimum in the intensity of the radiation.

The radiation pattern control means are further adapted to impose on all the introduced radiation patterns an identical time-varying phase component thereby changing the spatial orientation of the direction of the steep phase change and the sharp minimum in the intensity of the radiation.

The time-varying pattern comprises radiation of a selected wavelength intensity modulated at a selected frequency. The radiation pattern control means are further adapted to control a selected frequency relationship between the modulated radiation patterns introduced from each of the input ports having to produce in at least one direction a steep phase change and a sharp minimum in the intensity of the radiation.

The time-varying pattern comprises radiation of a selected wavelength intensity modulated at a selected frequency. The radiation pattern control means are further adapted to control a selected amplitude relationship between the modulated radiation patterns introduced from each of the input ports having to produce in at least one direction a steep phase change and a sharp minimum in the intensity of the radiation.

The radiation pattern control means are further adapted to add to all the introduced radiation patterns an identical time-varying amplitude component thereby changing the spatial orientation of the direction of the steep phase change and the sharp minimum in the intensity of the radiation.

The radiation is modulated at a frequency that enables resolution of the phase shift that originates during migration of photons in the subject.

The frequency is on the order of $10^8$ Hz.

The processing means further adapted to determine the phase or the intensity of the radiation altered by scattering and absorption in the subject.

The wavelength of the radiation is susceptible to changes in an endogenous or exogenous tissue pigment of the subject.

The gradient in photon density may also be achieved by encoding the introduced radiation patterns with a selected difference in their relative amplitude, relative phase, relative frequency or relative time.

Other advantages and features of the invention will be apparent from the following description of the preferred embodiment and from the claims.

DESCRIPTION OF THE PREFERRED EMBODIMENTS

Figure 1:
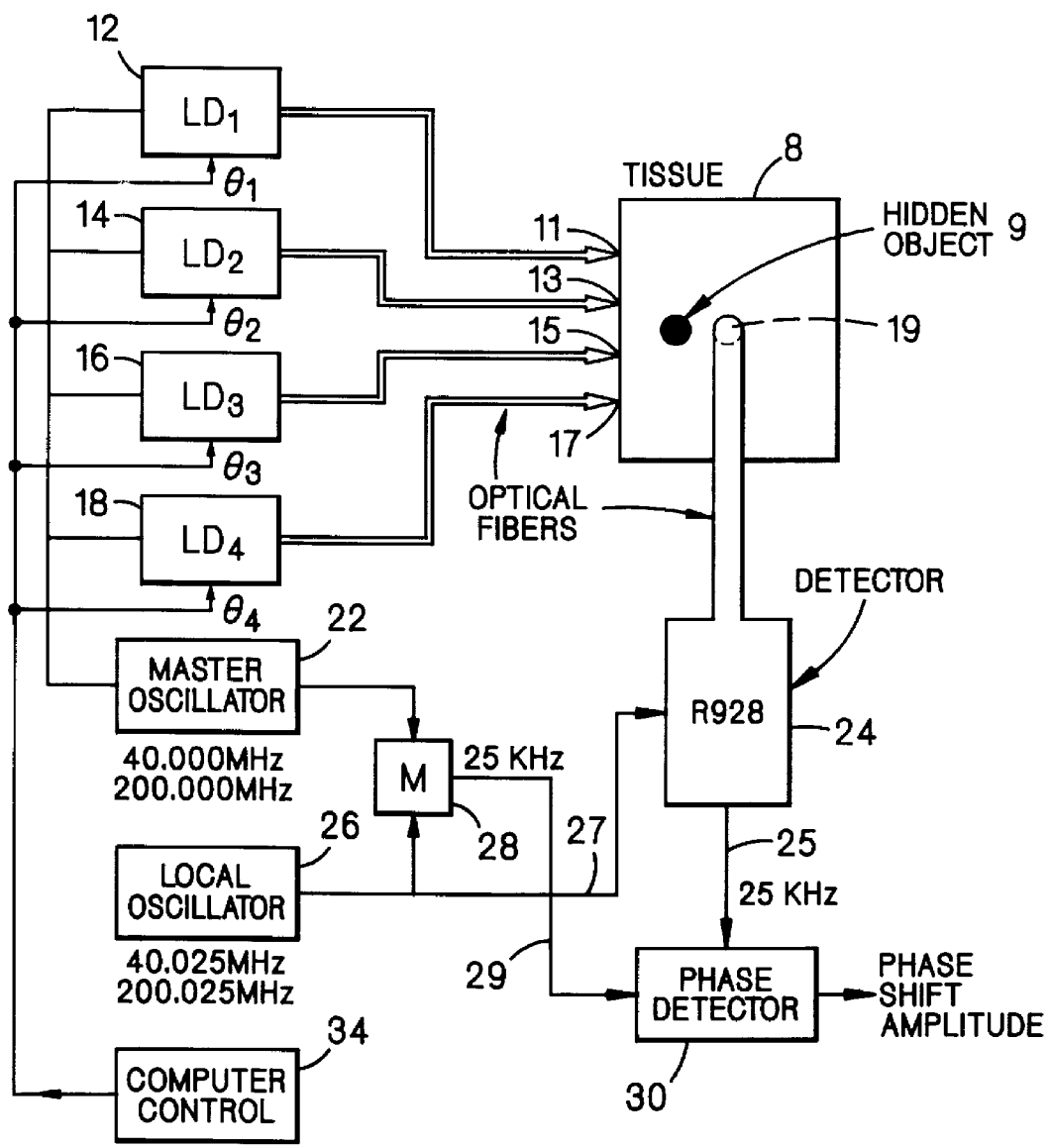
FIGS. 1, 1A and 1B show diagrammatically phase modulation imaging systems employing several input ports and one detection port in accordance with the present invention.
Figure 2:
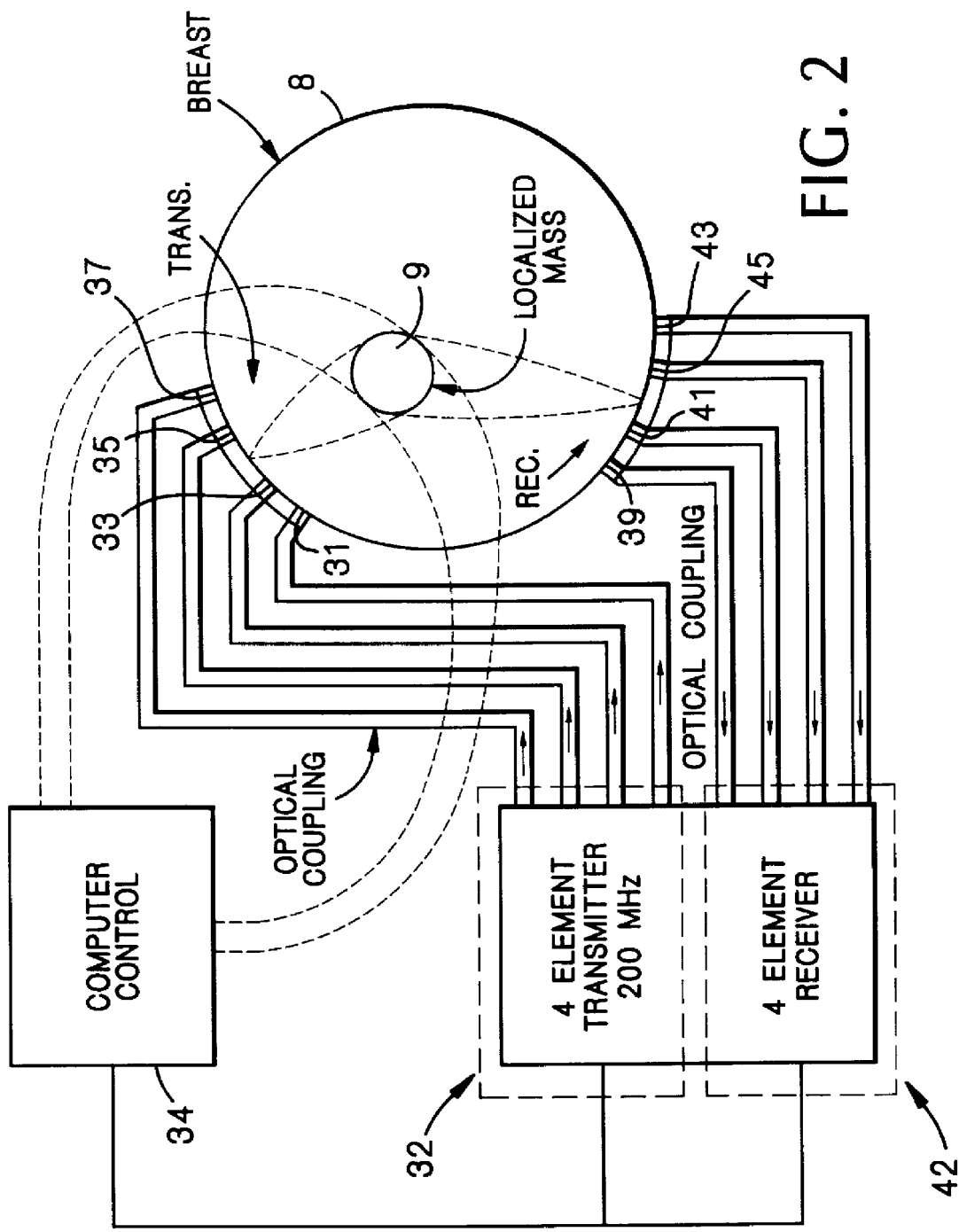
FIG. 2 is a block diagram of the phase modulation imaging system including several input ports and several detection ports in accordance with the present invention.
Figure 2A:
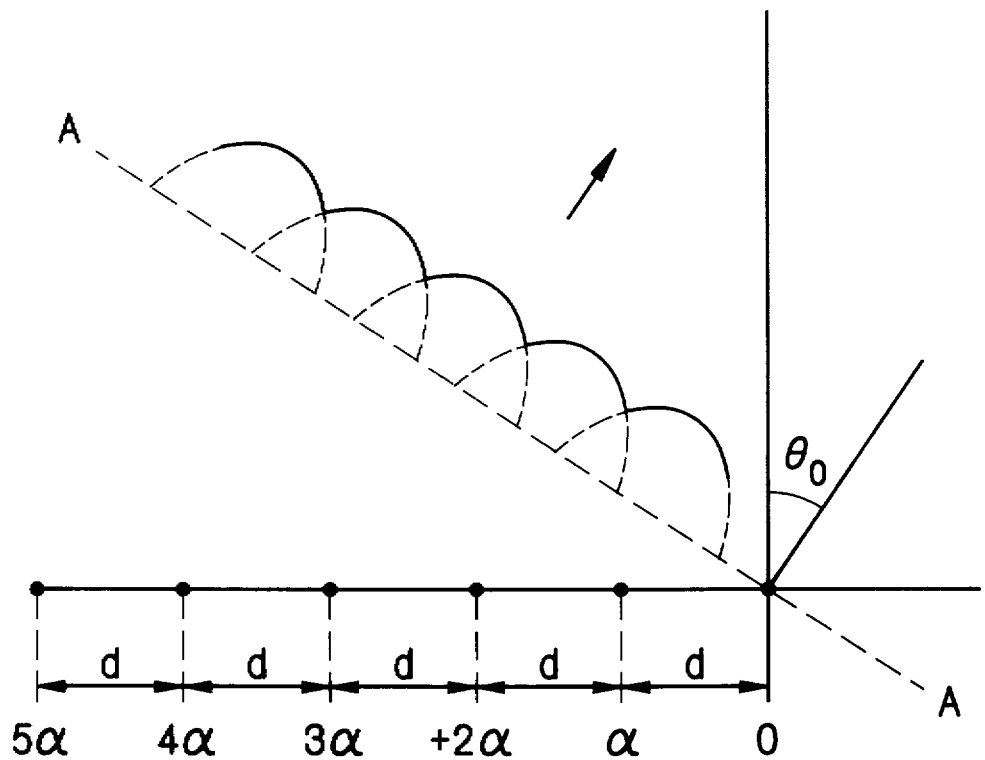
FIG. 2A depicts a phased array transmitter that radiates a directional beam.
Figure 2B:
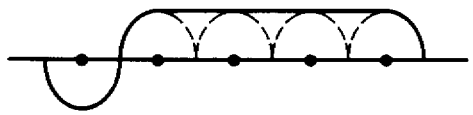
FIG. 2B depicts sequencing of the phases of an antiphase multi-element array to achieve an electronic scan of the photon density gradient in accordance with the present invention.
Figure 2B:
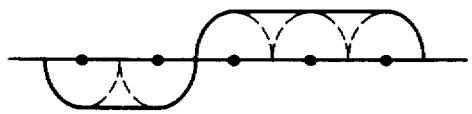
Figure 2B:
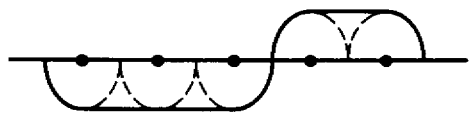
Figure 2B:
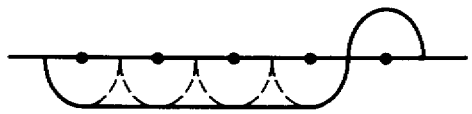
Figure 3:
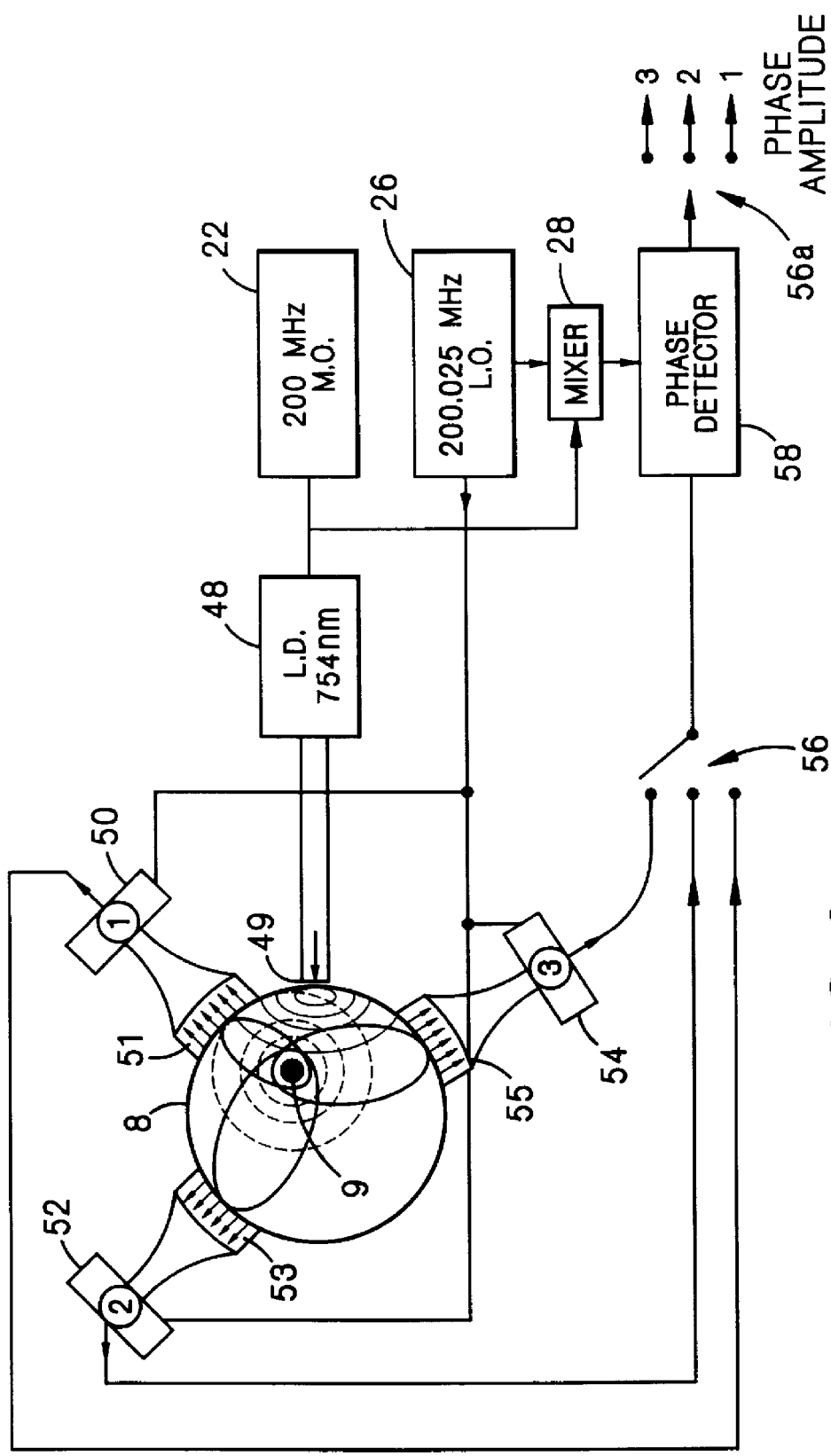
FIGS. 3 and 3A depict an imaging system for detection of a hidden fluorescing object in accordance with the present invention.

Imaging system embodiments of the present invention based upon interference effects of radiation migrating in a subject having scattering and absorptive properties are shown in FIGS. 1, 2, and 3. The systems effectively utilize, in this scattering medium, a directional beam of visible or IR radiation generated and/or detected by an array of sources and/or detectors, respectively. For instance, in the case of an array of sources, each source is placed at a selected location in the array and emits intensity modulated radiation, preferably coherent radiation from a laser diode, of a selected intensity and phase. The criteria for selecting the source locations, the intensities, and the phases of the respective sources is the shape of the desired beam that at any time point possesses a substantial photon density gradient produced by interference effects of radiation from the various sources. This gradient of photon density is localized and has directional properties. Overall, the resulting radiation formed by interference of the radiation of the individual sources migrates in a selected direction in the subject. In an antiphase system, the wavefront of the beam has sections of equal photon density separated by a sharp localized change in photon density. Selected different locations of the photon density gradient are shown in FIG. 2B.

In general, the wavefront propagates in the selected direction in the subject and the gradient of photon density is localized in one or more planes extending from the source array in a selected direction. If the subject includes a localized object having different scattering and absorptive properties from those of the surrounding environment, the propagating radiated field is perturbed. This perturbation is detected and from the source detector geometry the perturbing object can be located.

Figure 1A:
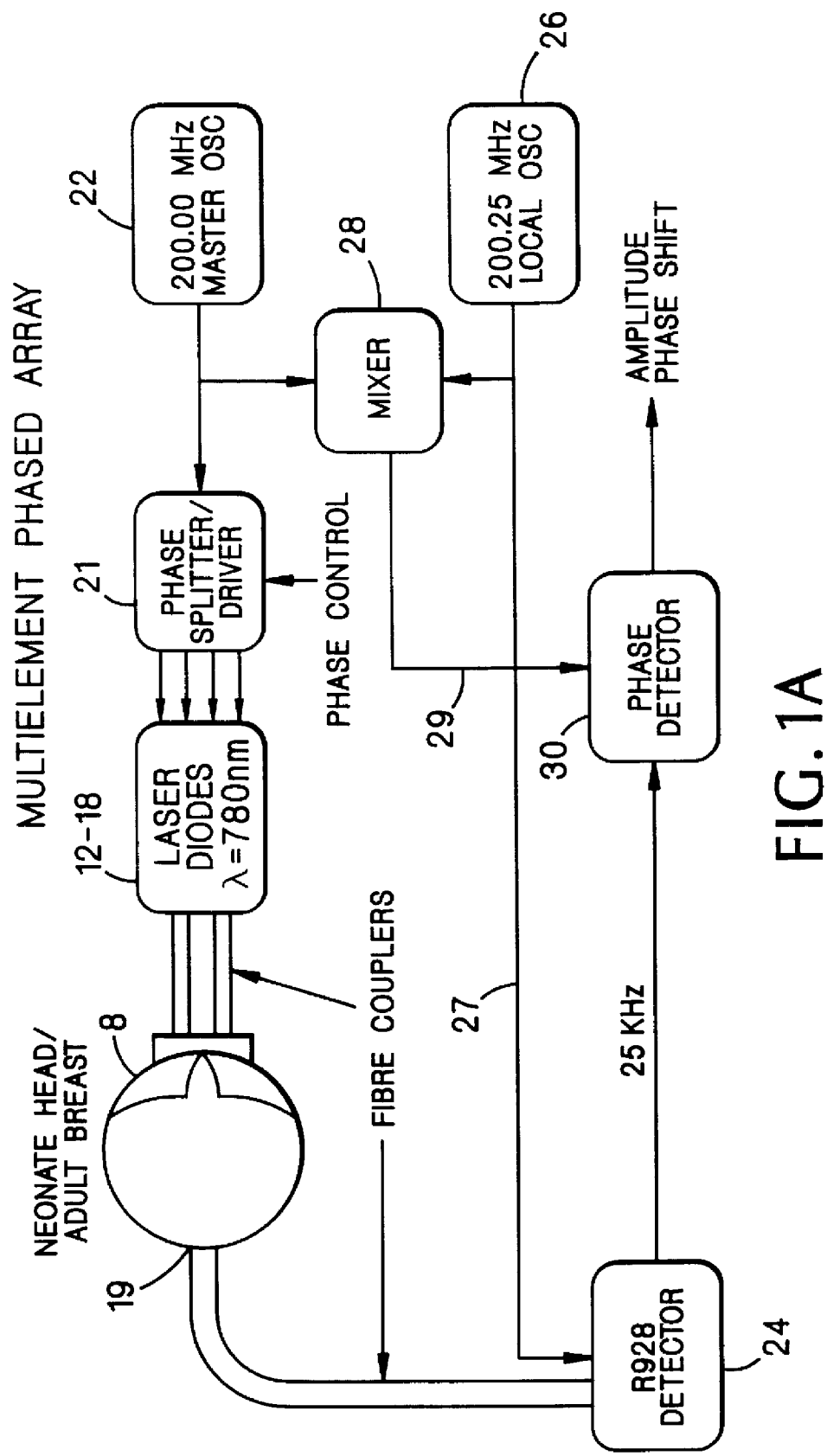

Referring to the embodiment of FIGS. 1 and 1A, the imaging system utilizes an array of laser diodes 12, 14, 16, and 18 for introducing light into the tissue at selected locations. The geometry of optical input ports 11, 13, 15, 17 and of an optical output port 19 is selected to examine a specific part of the tissue. From the known geometry of the optical input ports and the detection port and from the shape of the introduced and detected radiation, a computer can locate a hidden object 9 of examined tissue 8 (for example, a head or breast). A master oscillator 22, which operates at 200 MHz, excites laser diodes 12 through 18, that emit light of a selected wavelength (e.g., 760 nm). The light from each laser diode is conducted to the respective input port placed on a subject via a set optical fibers. A detector 24 detects the light that has migrated through the examined tissue. Preferably, detector 24 includes a photomultiplier tube (e.g., Hamamatsu R928) powered by a high voltage supply which outputs about 900 V in order to ensure a high gain. A local oscillator 26 operating at a convenient offset frequency (e.g., 25 kHz) sends a signal to a mixer 28 and a reference signal to detector 24. Accordingly, an output waveform 25 from detector 24 is at a carrier frequency equal to the difference of the detected and reference frequency, i.e., 25 kHz.

Detector 24 (for example, PMT Hamamatsu R928 or Hamamatsu R1645u) detects the scattered and absorbed light that has migrated through the subject. Detection port 19 is located several centimeters from the location of the input ports. The PMT detector is connected to the subject by the fiber optic guide, or, alternatively, may be directly placed on the subject. It has been found that the most cost-effective detector for measuring signals of frequencies on the order of $10^8$ Hz is Hamamatsu R928. However, the Hamamatsu R1645u detector is preferred due to its high precision. The second dynode of the PMT of detector 24 is modulated by 200.025 MHz signal 27 so that the 25 kHz hetrodyned signal 25 is received by a phase detector 30. Phase detector 30 also receives reference signal 29 from mixer 28. If phase detector 30 is a lock-in amplifier then the output signals are the phase shift and the intensity of the detected signal. Both the phase shift and the intensity of the detected light characterize the migration path of photons in the subject (e.g., the brain tissue).

Alternatively, a tunable dye laser or other laser source connected to a wide band acousto-optical modulator operating at the carrier frequency, e.g., 200 MHz can be used instead of the laser diode. The acousto-optical modulator modulates the intensity of the light emitted by the laser at the selected carrier frequency.

The invention also envisions using only one source of coherent light that irradiates one end of several optical fibers at the same time. The other end of each fiber is placed on the subject at a selected input port location. This source radiates light of a selected time varying pattern. The phase relationship and the intensity of the light carried by each fiber is varied by creating a time delay (e.g., different fiber length) and by coupling different amounts of light into each fiber.

Figure 1B:
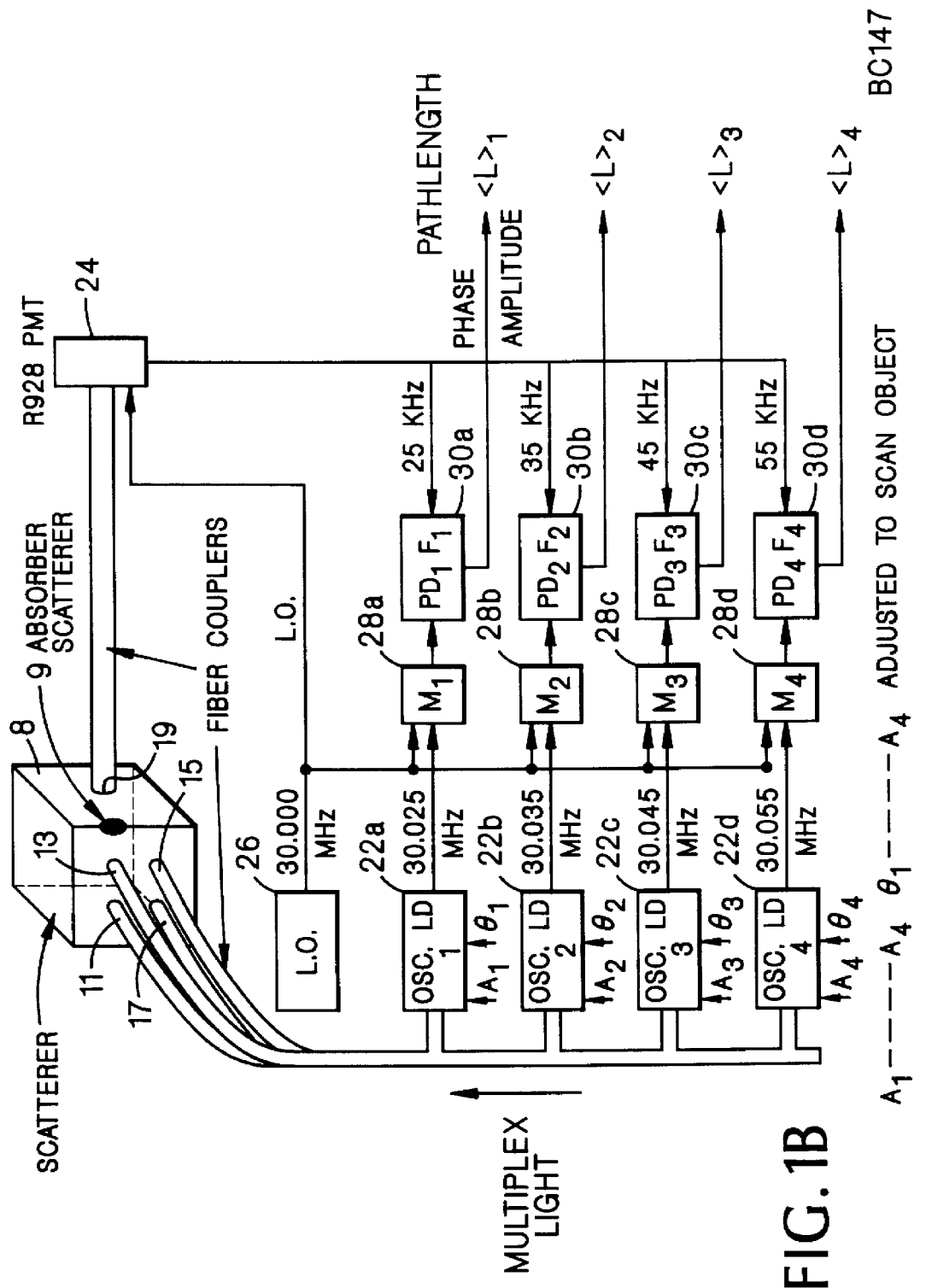

FIG. 1B shows diagrammatically an imaging system of FIG. 1 further adapted to encode the transmitted light using an offset frequency. Oscillators 22a, 22b, 22c and 22d drive four laser diodes at frequencies 30.025 MHz, 30.035 MHz, 30.045 MHz and 30.055 MHz, respectively. The laser diodes introduce the light that migrates in tissue 8 and is collected at detection port 19 and detected by PMT detector 24. Local oscillator 26 provides a 30 MHz reference signal to detector 24 that outputs a detection signal having 25 kHz, 35 kHz, 45 kHz and 55 kHz frequency components. Each component signal is phase detected at a corresponding phase detector (30a, 30b, 30c and 30d) having a suitable frequency filter. The phase detectors provide a phase shift, migration pathlength and amplitude for each frequency.

The imaging systems of FIGS. 1, 2, and 3 are shown to have a light source of a single wavelength; however, a dual wavelength imaging system is also envisioned according to this invention. In the dual wavelength imaging system two laser diodes or a tunable wavelength laser generate light of two wavelengths that is coupled to an optical fiber. Such a system will now be described.

Figure 4:
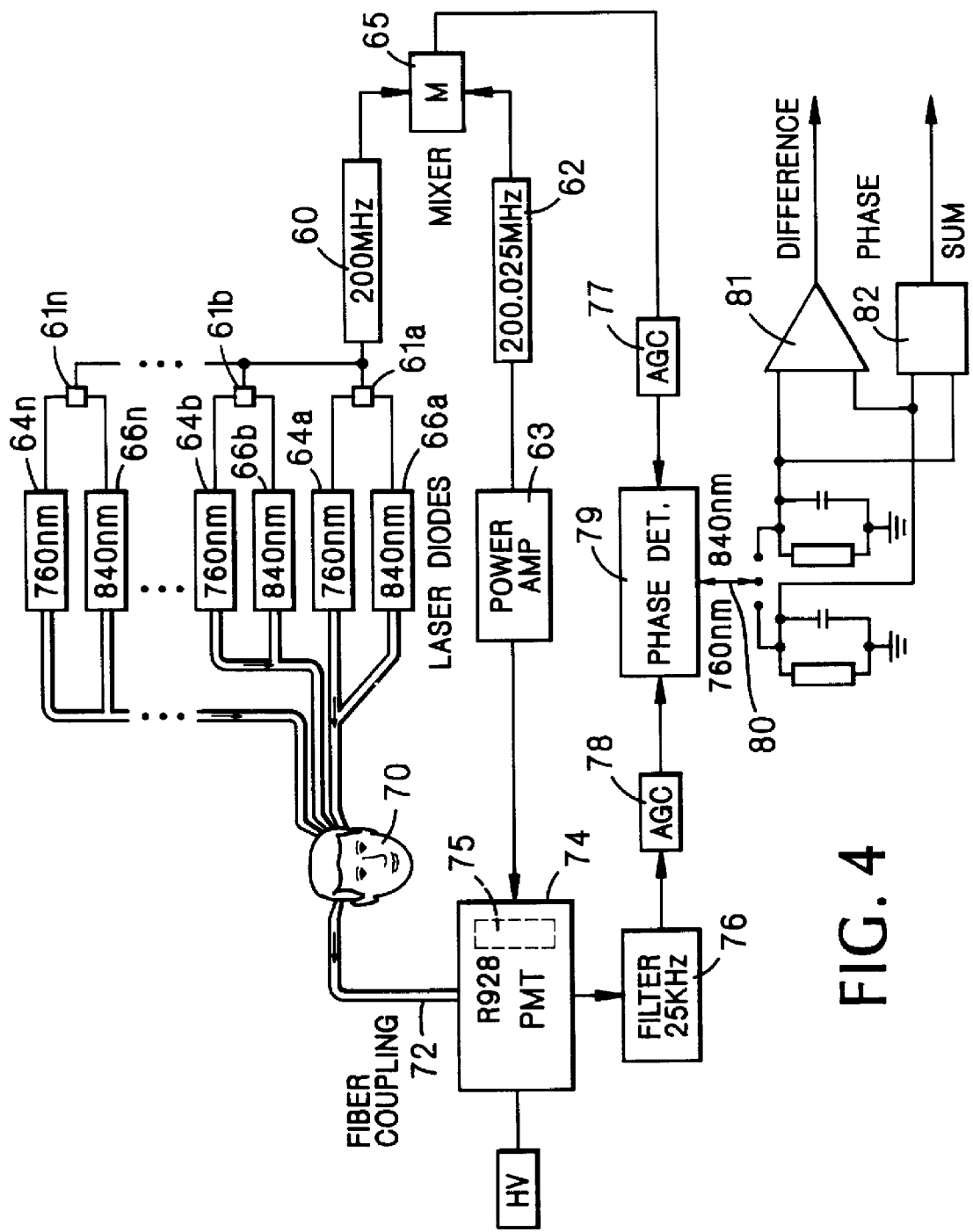
FIG. 4 is a block diagram of an alternative embodiment of a dual wavelength PMS system.

A dual wavelength operation is shown in FIG. 4. The system includes a master oscillator 60 operating at 200 MHz and an oscillator 62 operating at 200.025 MHz which is offset 25 kHz from the master oscillator frequency. The offset frequency of 25 kHz is a convenient frequency for phase detection in this system; however, other offset frequencies as high as a few megahertz can be used. Oscillator 60 alternatively drives two sets of laser diodes 64a, 64b, ..., 64n and 66a, 66b, ..., 66n using switches 61a, 61b, ..., 66n. These switches are driven electronically to couple a selected wavelength into the optical fiber and also to achieve a selected radiation pattern resulting from the radiation emanating from the individual fibers. An output 8 mm fiber coupler 72 collects photons for an R928 PMT detector 74. The second dynode (shown in FIG. 3B) of PMT 74 is modulated with a 200.025 MHz reference signal generated by oscillator 62 and amplified by an amplifier 63. Thus, the output signal of the PMT detector has a frequency of 25 kHz. PMT detector 74 alternately detects light of the two laser diodes that has migrated in the tissue and produces corresponding output signals, which are filtered by a filter 76 and leveled by an automatic gain control (AGC) circuit 79. A reference signal of 25 kHz is produced in a mixer 65 by mixing the 200 and 200.025 MHz oscillator signals. The reference 25 kHz signal is also leveled using the second AGC 77 and fed into a phase detector 79. Phase detector 79 generates a signal indicative of the phase of each output signal relative to the phase of the reference signal. The outputs of phase detector 79 are alternately selected by an electronic switch 80, filtered, and then input to an adder 82 and a subtractor 81 to produce sum and difference signals proportional to $<L>_{\lambda_1}+<L>_{\lambda_2}$ and $<L>_{\lambda_1}-<L>_{\lambda_2}$. The difference and sum signals are then used to calculate changes in the probed pigment and in the blood volume, respectively.

Figure 4A:
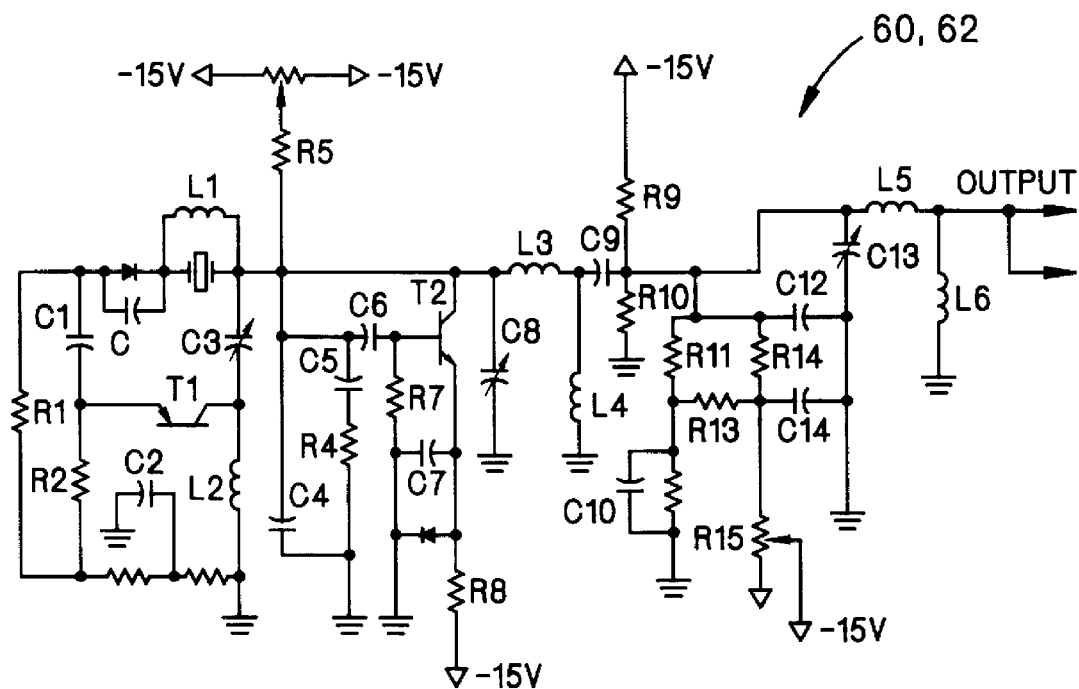
FIG. 4A is a schematic diagram of an oscillator circuit of FIG. 4.

A schematic diagram of preferred oscillator 60 or 62 is shown in FIG. 4A. This circuit has a drift of only 0.03 degrees/hr. (Weng, et al., "Measurement of Biological Tissue Metabolism Using Phase Modulation Spectroscopic Measurement," SPIE, Vol. 143, p. 161, 1991, which is incorporated herein by reference). The crystal is neutralized, which enables operation at resonance, and thus achieves long-term stability. The respective crystals of oscillators 60 and 62 are offset from each other by 25 kHz. This circuit provides a sufficient output to directly drive a 5 mW laser diode.

Figure 4B:
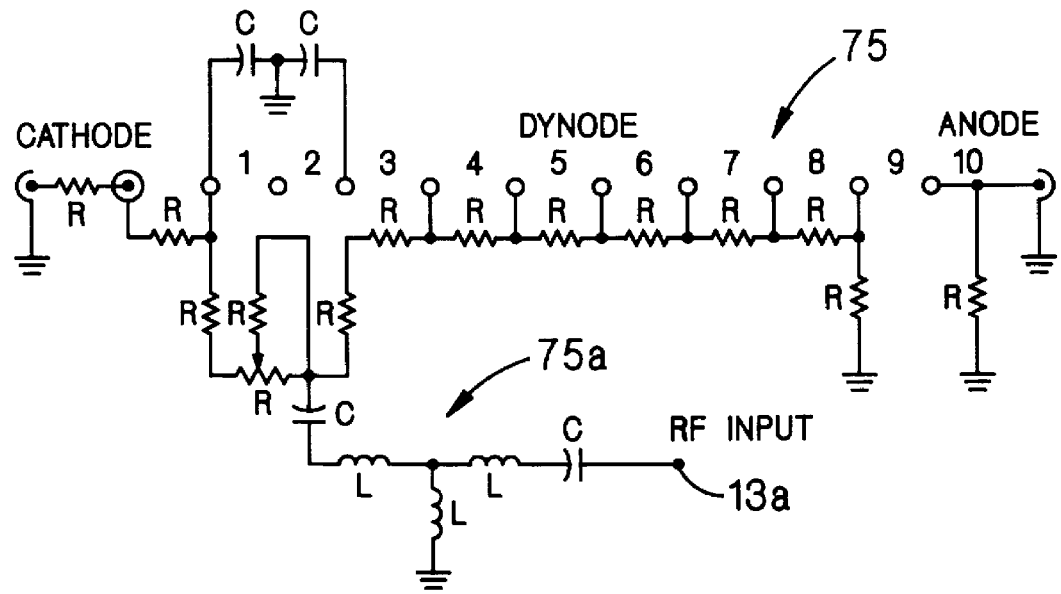
FIG. 4B is a schematic diagram of a PMT heterodyne modulation and mixing network shown in FIG. 4.

A modulation circuit 75 for the second dynode of the PMT is shown in FIG. 4B. This circuit uses a resonant circuit 75a with an impedance of 20,000 ohms instead of the usual 50 Ω load with very high power dissipation, providing a 50 V drive of the photomultiplier dynode while dissipating only a few watts of power.

Figure 4C:
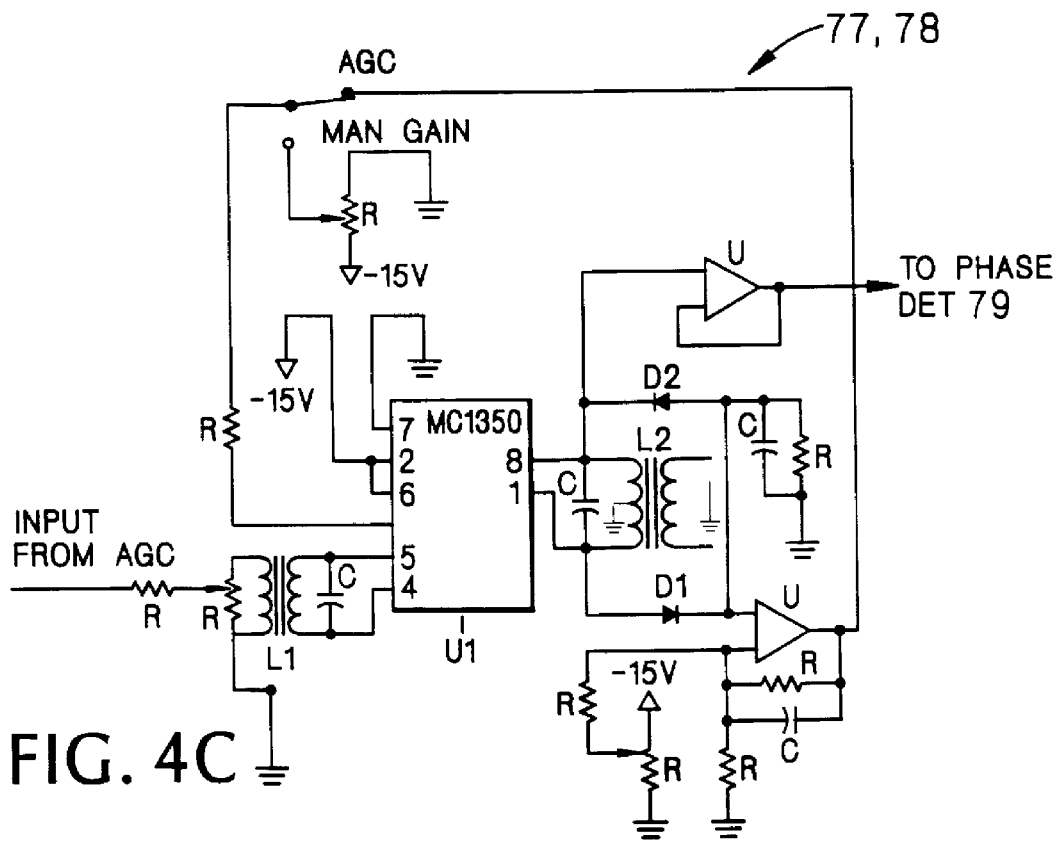
FIG. 4C is a schematic diagram of an AGC circuit shown in FIG. 4.

To obtain stable operation of the phase detector, a stable input signal is required. The 25 kHz AGC circuit 77, 78 illustrated in FIG. 4C includes an MC 1350 integrated circuit U1, featuring wide range AGC for use as an amplifier. The signal amplitude is controlled by a feedback network, as shown. A major reason for the accurate detection of phase changes by the PMT system is that the phase detector input signal level is kept nearly constant by the AGC circuit. Since the input voltage change of between 2 and 6 volts causes variation in the phase shift of only 0.2%, the AGC circuit eliminates the need for a very stable high voltage power supply.

Figure 4D:
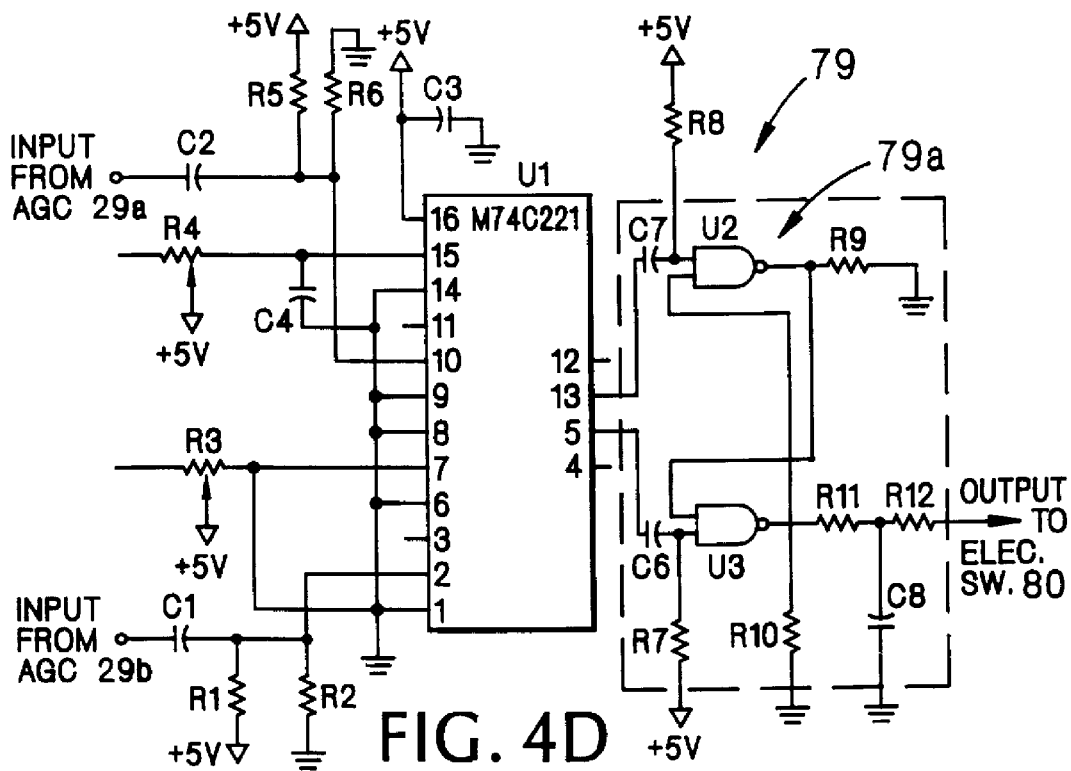
FIG. 4D is a schematic diagram of a phase detector circuit shown in FIG. 4.

A preferred phase detector circuit is shown in FIG. 4D. Two sinusoidal signals (the measurement signal and the reference signal) are transformed to a square wave signal by a Schmitt trigger circuit 79a. The phase of the square wave signal is shifted by an RC change (composed of R11, R12, C8), which makes it possible to change the measuring range. The detector further includes a 74HC221 integrated circuit. The lock-in amplifier technique obtained to derive the difference of the phase and amplitude of the two signals has the highest signal to noise ratio possible for this type of equipment.

The above-described systems utilize the carrier frequency on the order of $10^8$ Hz which is sufficiently fast to resolve the phase shift of the detected light. The characteristic time, the time it takes for a photon to migrate between an input port and an output port, is several nanoseconds. The sensitivity of the system is high, approximately 70° per nanosecond or 3° per centimeter change of pathlength, as observed in experimental models. Selection of the modulation frequency also depends on the desired penetration depth and resolution of the imaging system that will be described below. If deep penetration is desired, a low modulation frequency (e.g., 40 MHz) is selected, and if shallow penetration is needed, modulation frequencies as high as $10^9$ Hz can be used.

Referring to FIGS. 1 and 1A, a master oscillator 22 operates at a modulation frequency in the range of 40 to 400 MHz selected according to the desired penetration depth of the optical field. The array of laser diodes 12, 14, 16, and 18 generates a highly directional radiation pattern, which is employed in the tissue examination.

In one preferred mode of operation, laser diodes 12 to 18 operate in a phased array pattern which is introduced into the tissue and detected by a single PMT detector 30. Master oscillator 22 operating at 200 MHz drives a multi-channel phased splitter which gives outputs at predetermined phases. Input ports 11 through 17 are located at selected distances and an appropriate phasing of the array creates a directional beam and enables scanning of the optical field in two dimensions across the tissue, as shown in FIGS. 2A, 2B, and 2D. After migrating through the tissue, the optical field is collected in a large area fiber on selected locations 19. The detected signals are heterodyned in the PMT detector 24 by utilizing the output of local oscillator 26, operating at a 25 kHz offset frequency, to detector 24. The resulting 25 kHz signal is phase detected with respect to the output signal 29 of mixer 28 and detector 24. Phase detector 30 outputs the phase and the intensity of signal 25. The detected phase shifts and intensities are stored and used for construction of an image of the subject. This is performed by computer control 34, which governs the operation of the system.

FIG. 2 depicts a phase modulation imaging system comprising an input port array for introducing radiation and a detection port array for detecting radiation that has migrated in the subject. The operation of the system is controlled by computer control 34, which coordinates a transmitter unit 32 with a receiver unit 42. Transmitter unit 32 comprises several sources of visible or IR radiation adapted to introduce a selected time-varying pattern of photon density into subject 8 by array of input ports 31, 33, 35, and 37. Receiver unit 42 detects radiation that has migrated in the subject from the input port array to an array of detectors 39, 41, 42, and 47.

The radiation sources of transmitter unit 32 are intensity modulated at a frequency in the range of 40 MHz to 200 MHz, as described for the imaging system of FIG. 1. Receiver unit 42 detects and processes the radiation using the same principles of the phase and amplitude detection as described above. The signal detected at individual ports can be phased using appropriate delays.

Several modes of operation of the transmitter array and receiver array are described in FIGS. 2A, 2B, 2C, and 2D. Referring to FIG. 2A, it has been known, that for a simple horizontal linear array of N identical elements radiating amplitude modulated light spaced a distance, d, apart. The radiating wavefront is created by the interference effect. If all elements radiate in phase the wavefront propagates in a direction perpendicular to the array. However, by appropriately phasing the radiating elements, the resulting beam can scan space in two dimensions. We consider the phases of the signal along the plane A—A whose normal makes an angle $\theta_0$ with respect to the array normal. The phase of the signal from the first radiator lags the phase of the second radiator by a phase angle $(2\pi/\lambda)d \sin \theta_0$ because the signal from the second radiator has to travel a distance $d \sin \theta_0$ longer than the signal from the first radiator to reach plane A—A. Similarly, the phase of the signal from the nth radiator leads that from the first radiator by an angle $n(2\pi/\lambda))d \sin \theta_0$. Thus, the signals from the various radiators can be adjusted to be in-phase along the A—A plane, if the phase of each radiator is increased by $(2\pi/\lambda)d \sin \theta_0$. Consequently, at a point on the wavefront in the far field of the transmitter array the signals from the N radiators will add up in phase, i.e., the intensity of the total normalized signal is a sum of the signals from the individual sources. The constructed pattern has a well defined directional characteristic and a well pronounced angular dependence, i.e., the transmitter pattern has a well defined transfer characteristic of the transmitter with respect to the angle $\theta_0$.

FIG. 2B depicts an arrangement of phases for the sources the system of FIG. 2 operating in one preferred mode of operation. The array of five sources is divided into two or more portions that are phased 180° apart. Each portion has at least one source. The sources of each portion radiate amplitude modulated light of equal intensity and are spaced so that the resulting beam of two or more equally phased sources has a substantially flat wavefront, i.e., no gradient of photon density. On the other hand, there is a sharp 180° phase transition, a large gradient in photon density between two antiphased portions of the array. Thus, the radiated field possesses an amplitude null and a phase transition of 180° (i.e. crossover phase), which is due to the large gradient of photon density.

Electronic scanning is performed by appropriately varying the apportionment of 0° and 180° phases on the sources. The five element array of FIG. 2B can have the 180° phase transition along four different parallel planes extending from the array. Scanning is achieved by electronically switching the sources by 180°, so that the photon density gradient moves in the direction parallel to the location of the sources.

Figure 2C:
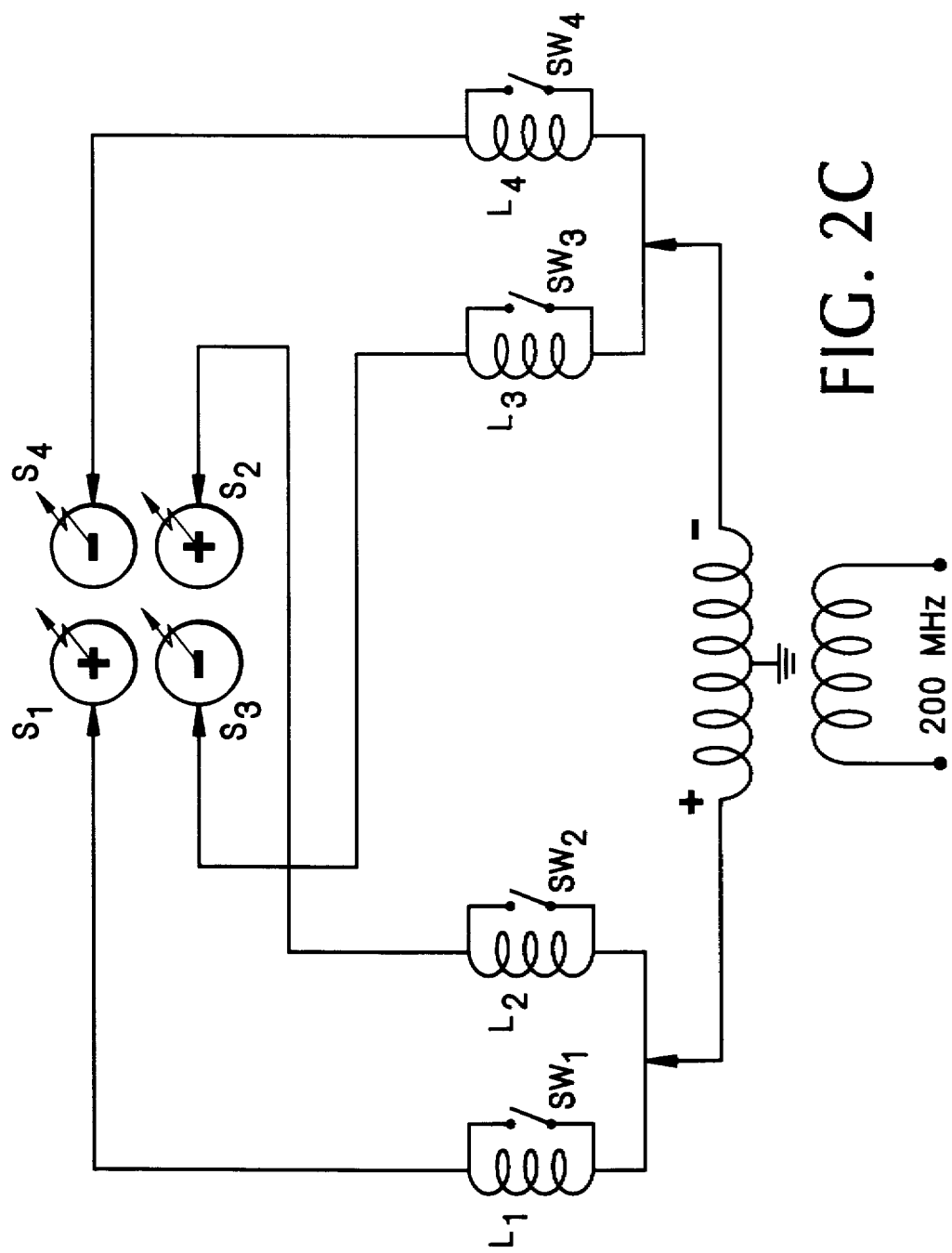
FIG. 2C depicts four element antiphased array designed for a conical scan of the photon density gradient in accordance with the present invention.
Figure 2D:
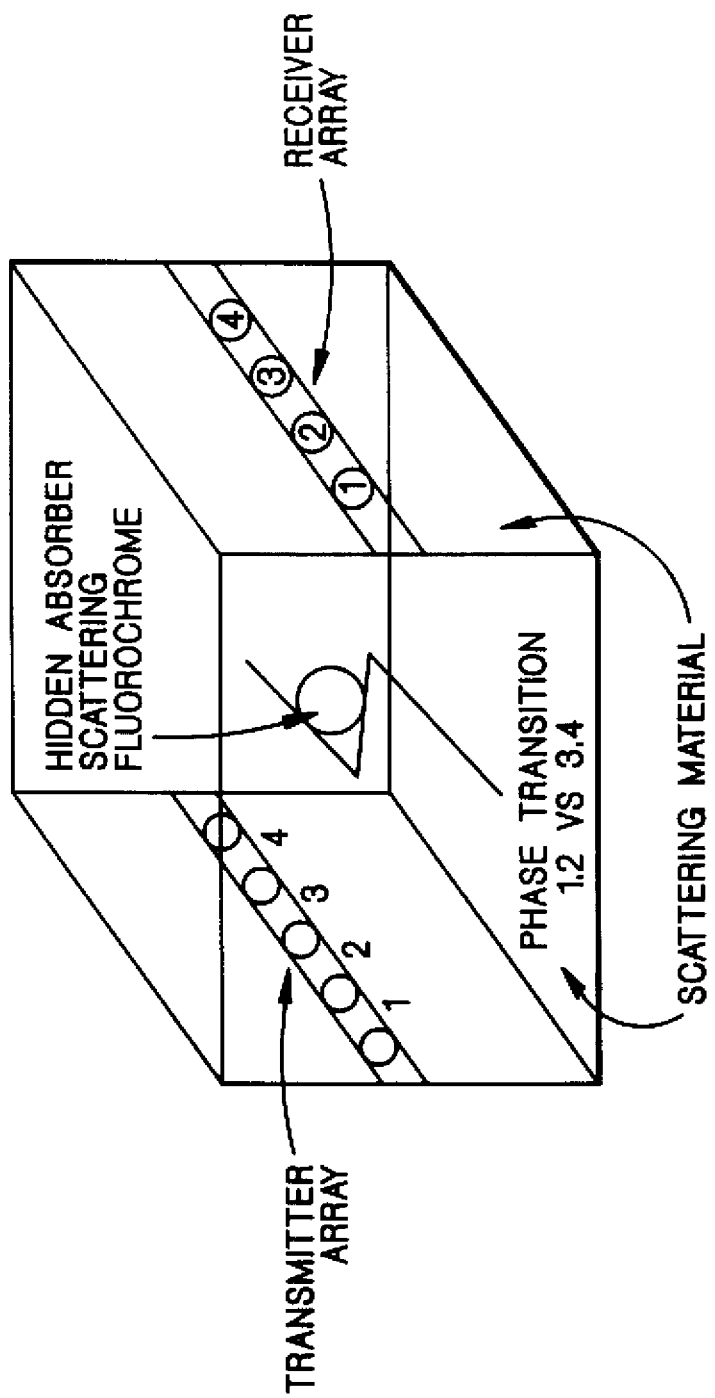
FIG. 2D depicts the input and output port arrangement of an imaging system in accordance with the present invention.

Using the principles described in FIGS. 2A and 2B, a conical scan of a directional beam possessing at least one substantial photon density gradient can be accomplished using a four element antiphased array, as shown in FIG. 2C. The laser diodes are antiphased using a push pull transformer. The phasing and amplitude of four laser diodes $S_1$, $S_2$, $S_3$, and $S_4$ arranged into a two dimensional array is modified sequentially using the switches $Sw_1$, $Sw_2$, $Sw_3$, and $Sw_6$ and inductances $L_1$, $L_2$, $L_3$, and $L_4$.

FIG. 2D shows a possible arrangement of the transmitter array and the receiver array. The above described directional beam enters subject 8 at the transmitter array location and is pointed to hidden absorber 9 which perturbs the migrating beam. The field perturbation is measured by the receiver array. Scanning of the transmitter array or the receiver array is envisioned by the present invention.

A hidden absorber that includes a fluorescent constituent is detected using a selected excitation wavelength of the laser sources of the transmitter array. Then, the radiation is absorbed, and almost instantly a fluorescent radiation of a different wavelength is re-emitted. The re-emitted radiation propagating in all directions is detected by the receiver array.

FIG. 3 depicts a phase modulation imaging system comprising one input port and several arrays of detection ports. This system operates comparably to the systems of FIGS. 1 and 2. The 754 nm light of a laser diode 48 is amplitude modulated using master oscillator 22. The light is coupled to subject 8 using an input port 49. The amplitude modulated light migrates in the subject and is scattered from hidden object 9. It is also expected that hidden object 9 has a different effective index of refraction than subject 8. The migrating radiation is governed by the laws of diffusional wave optics that are described below. The scattered radiation migrates in several directions and is detected by detection systems 50, 52, and 54.

Ports 51, 53, and 55 of the detection systems can include either large area fibers or arrays of detection ports. If large area fibers are used then detector systems 50, 52, and 54 correspond to detector 24 of FIG. 1. If arrays detection ports are used, then each of detector systems 50, 52, and 54 includes several individual PMT detectors. The PMT detectors of each detector system are phased utilizing a selected phase mode, as described above. The phasing is controlled by the computer control. The detected signals are heterodyned at the PMT detectors and sent to a phase detector 58. Phase detector 58 detects alternatively the heterodyned signals using a switch 56. Operation of phase detector 58 is similar to the operation of phase detector 30 of FIG. 1. The detected phase and amplitude are alternatively sent to the computer control using a switch 56a. Even though only one phase detector is shown in FIG. 3, the invention envisions use of several phase detectors.

If hidden absorber 9 includes a fluorescent constituent, laser diode 48 is selected to introduce an excitation wavelength (e.g., 754 nm). The introduced, intensity modulated radiation, excites the fluorescent constituent which re-emits radiation in all directions, as shown in FIG. 3. The re-emitted radiation is detected using detector systems 50, 52, and 54. To increase the system resolution, each detector can be furnished with an interference filter selected to pass only the fluorescent radiation.

Figure 3A:
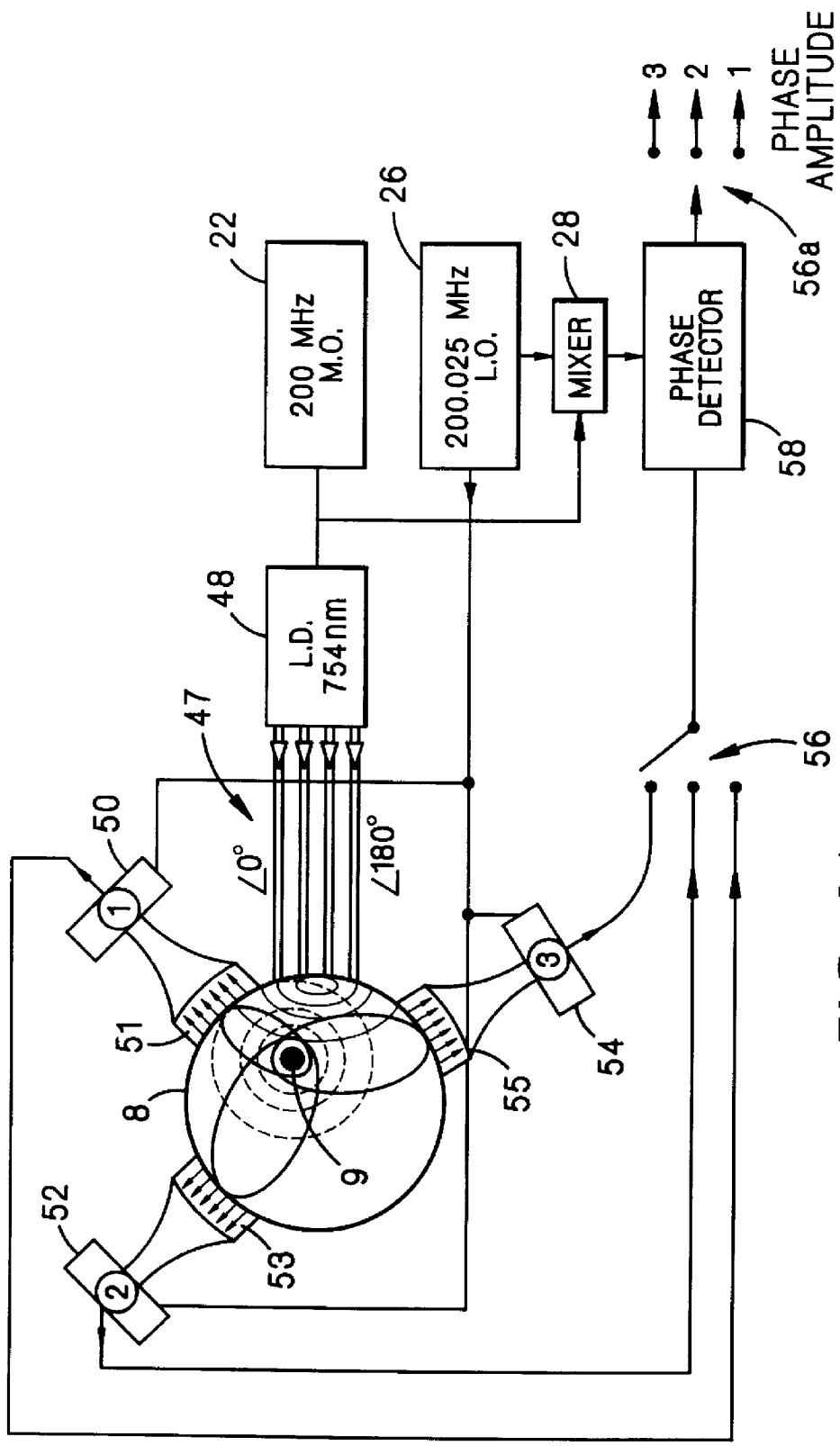

FIG. 3A shows diagrammatically an imaging system used for detection of a fluorescing object 9. The system is a modified version of the system of FIG. 3 wherein a four element phase array 47 introduces a 200 MHz light of a 0° and 180° phase. The diffusion wave emitted from array 47 is re-emitted by object 9 and detected by ports 51, 53 and 55 and processed as described in connection with FIG. 3. Array 47 effectively codes the illumination light. Thus, when array 47 is rotated about the examined organ with object 9, the receivers will contain information corresponding to the orientation of the object. Each detection port also includes a filter that passes only the fluorescent radiation; this improves the resolution of the system.

The interference of several waves, as described in FIG. 2A, has been long known in a non-scattering medium, wherein the radiation propagates on a straight line, but not in a strongly scattering medium. Referring to FIGS. 6, 6A, 6B, and 6C, in a simple experiment, interference of two different diffusive waves in a strongly scattering medium was demonstrated. Propagation of visible IR radiation in a scattering medium such as tissue can be described by diffusion of photons, and thus we describe it as a diffusive wave that exhibit refraction, diffraction and interference. The diffusive waves, which can be visualized as "ripples of brightness," represent a scalar, over-damped traveling waves of light energy density.

Figure 6:
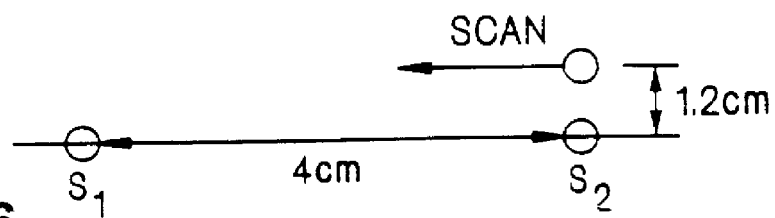
FIG. 6 shows an experimental arrangement of a two element phased array used in an interference experiment.
Figure 6A:
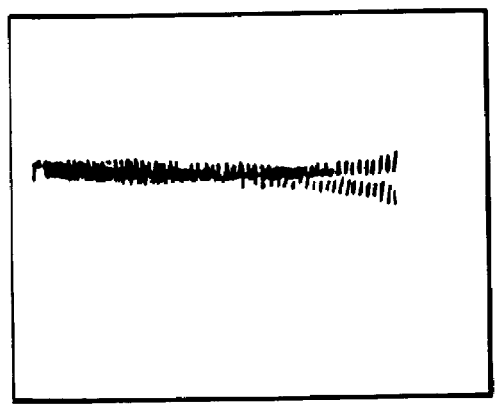
FIGS. 6A, 6B, and 6C show detected interference patterns of two diffusive waves.
Figure 6B:
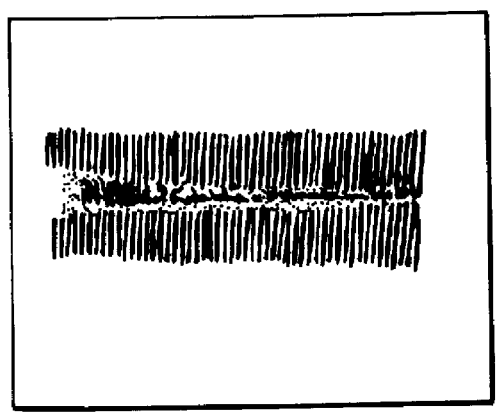
Figure 6C:
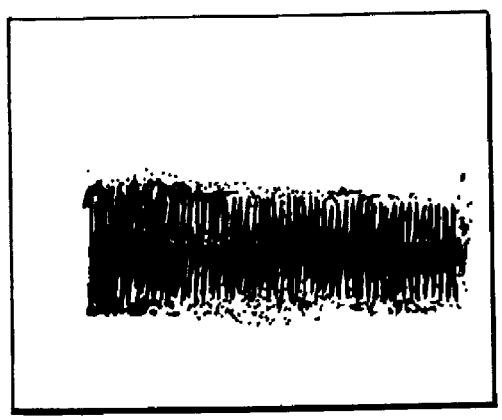
Figure 7:
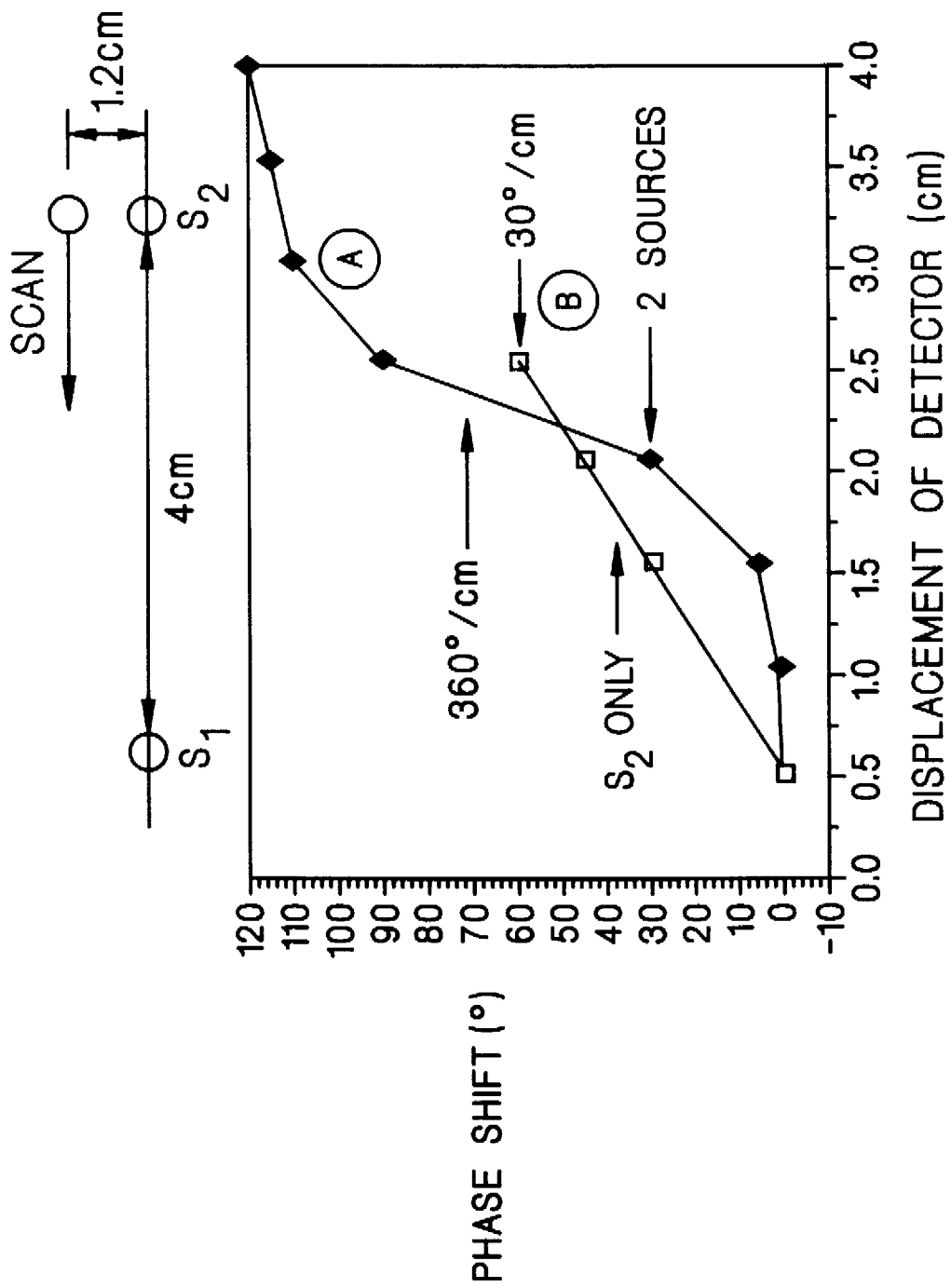
FIG. 7 displays the phase shifts measured for a two element array (curve A), and for a single source (curve B).

Referring to FIG. 6, the two laser diodes were separated at a distance of 4 cm and 1.2 cm from the detection port. The intensity modulated light of the two laser diodes at frequency 200 MHz was sent through two optical fibers to a container with an Intralipid™ suspension. The source detector distance was varied by moving the optical port of the detection fiber along a line parallel to the position of the sources. FIGS. 6A, 6B, and 6C show measured maxima and minima of the optical field migrating in the medium. This data demonstrates interference between two diffusive waves created by two coherent emitting sources of phase difference 180 degrees. FIG. 7 summarizes the experiment, wherein the displacement of the detector is plotted against the phase shift measured by the detector. The phase shift displays the steepest part of the trace, curve A, (slope of about 360°/cm) at the displacement of about 2.25 cm. Curve B is measured with an optical field of source. $S_2$. Here, the measured slope is about 30°/cm. When comparing curves A and B we demonstrate much higher sensitivity of the null detection of the two element array contrasted with a diminished sensitivity to the detector displacement when using a single source arrangement. The sensitivity of the two source arrangement is increased by about a factor of 10. The sensitivity is further increased when using four or more element phased array, which sharpens the photon density gradient and thus provides a higher resolution for locating the hidden object.

In a strongly scattering medium, the emitted photons undergo a large number of collisions and their migration can be determined by applying the diffusion equation. The diffusion equation for photons in a uniformly scattering medium was solved by E. Gratton et al., "The possibility of a near infrared optical imaging system using frequency domain methods." in Mind Brain Imaging Program, Japan 1990; and by J. Fishkin et al., "Diffusion of intensity modulated near-infrared light in turbid media", SPIE Vol. 1413 (1991) p. 122. A solution of the diffusion equation was obtained for the light of a point source (at r=0) radiating $S\{1+M \exp[-i(\omega t+e)]\}$ photons, wherein S is the source strength (photons/sec.), M is the modulation of the source at frequency $\omega$, and e is an arbitrary phase. The photon intensity can be calculated as $$I(r,t)=c^*\rho(r,t),$$

wherein $\rho(r,t)$ is the photon density and $c=10^8$ m/s is the velocity of light.

When solving the diffusion equation using a spherical-harmonics approximation in a non-absorbing medium for the density of photons $\rho(r,t)$ than $$I(r,t)=(I_0/Dr)+(I_0/Dr) \exp [-r(\omega/2cD)^{1/2}]\exp [ir(\omega/2cD)^{1/2}-i(\omega t+e)],$$

wherein the diffusion constant D is ⅓ of the mean free path. In the absence of an amplitude modulated signal ($\omega=0$) the solution corresponds to a spherical wave propagating without attenuation. For a non-zero frequency, the amplitude of the signal at a frequency $\omega$ decreases exponentially. The light wave front the emitted advances at the constant velocity V $$V=(2Dc\omega)^{1/2}$$

and has wavelength $$\lambda=2\pi(2cD/\omega)^{1/2}$$

The above equations show that higher modulation frequencies yield shorter effective wavelengths, and smaller diffusion constants also give shorter effective wavelengths. In principle, short wavelengths can be obtained using high frequency modulated waves in a very turbid medium. However, the amplitude of the modulated wave decreases exponentially with the modulation frequency. Therefore, the best resolution, i.e., the shortest wavelength, is obtained using the highest frequency which still gives a measurable signal. The diffusion process limits the penetration depth at any given modulation frequency, because of the exponential decrease of the wave's amplitude, and also decreases the velocity of light propagation.

The above described diffusion wave approach treats amplitude modulated light waves in scattering media using the framework of wave optics. The photon intensity, calculated as superposition of different waves, constitutes a scalar field, propagating at a constant velocity. At any given modulation frequency, the wave optics phenomenology of scalar fields is valid. Therefore, in the frequency-domain, the measurement and analysis of light diffusing in tissues from several sources will undergo constructive and destructive interference. Furthermore, wave refraction occurs at a boundary between two different tissues. It causes a deviation of the direction of propagation of the wave front, and thus there is a change in the amplitude and phase shift of the propagation wave. The direction change is a function of the ratio of the effective index of refraction in the two tissues. In diffusional wave optics, on the other hand, the wave's amplitude is exponentially attenuated as the wave propagates in the scattering medium. This attenuation is in addition to the exponential attenuation caused by finite absorption of the medium.

Amplitude modulated waves propagate coherently in the scattering medium; this is crucial for image reconstruction. It is possible to accurately measure in real time, the average intensity, amplitude, and phase of the wave front over a large area using a single detector or an array of detectors applying well-established frequency-domain methods.

The emitters are varied sequentially in phase starting with the first emitter in the line and followed by subsequent emitters. Each emitter emits a spherical wave and propagation of the resultant beam is perpendicular to the wavefront. If all the transmitter delays are equal, the beam travels straight ahead. Delay lines which produce variable transmitter delays can be used to obtain appropriate phasing for steering the beam across the tissue. The same principle can apply during reception.

There are two important aspects of imaging as envisioned by the present invention. The first is a geometrical aspect and the second is phasing of the transmitters and receivers.

It is also possible to construct a two-dimensional array for two-dimensional pointing (e.g., FIG. 2C). The multiplexing switches used with these arrays can be constructed as an integral part of the array and can consist of field effect transistors arranged so that access to any element may be obtained by the application of two adverse signals.

In addition to electronic scanning, the two-dimensional scanning can be achieved by moving the array of sources and detectors in a regular pre-determined pattern in a plane parallel to that being investigated in the subject. For maximum detection, the detector is places in the plane of the photon density gradient of the resulting field created by the array of sources. The plane of the photon density gradient is swept as the array moves. In this sweeping action, as a strongly or weakly absorbing object enters the radiation field, the detector registers a field imbalance due to the above described refraction of the propagating radiation. A two-dimensional image is formed by storing the information while the probe is moved across the subject. Several scans in different imaging planes are envisioned by the invention. If the system is duplicated or time shared in two other faces of a cube, an algorithm would be used to provide a 3-dimensional picture of the object by triangulation. For a linear array of sources, there is a plane in which the null is sensitively detected, and the intersection of three planes (particularly at orthogonal intersection) defines the location of a hidden absorber. The data storage is accomplished electronically.

The detector detects the intensity and the phase shift of the radiation that has migrated in the subject. The phase shift depends on the tissue properties, i.e., absorption and scattering. For the low frequencies the phase shift is proportional to $((1-g)\mu_s/\mu_a)^{1/2}$ and for the high frequencies proportional to $1/\mu_a$. To obtain desired penetration depth, appropriate frequency for both master oscillator 22 and local oscillator 26 is chosen; however, the phase relationship of the laser diodes is maintained.

Different types of phased arrays are designed for optimal examination and imaging of different human organs (e.g., human head or breast). For example, a mosaic of optical input ports and optical detection ports defined by positions of optical fibers attached to a skull cap may be used. A standardized mapping may be developed also using x-ray techniques. Contrast labeling of different physiological structures will aid the visualization and orientation. The amplitude and phase of the signals can be monitored on a precision oscilloscope. In order to scan the phased array past a fixed object of approximately known position, as in needle localization procedures, the location of the input and output ports will be scanned past the object and the position of maximum phase shift will be recorded in one-dimension; however, detection in two and three dimension can be performed in the same way.

Figure 8A:
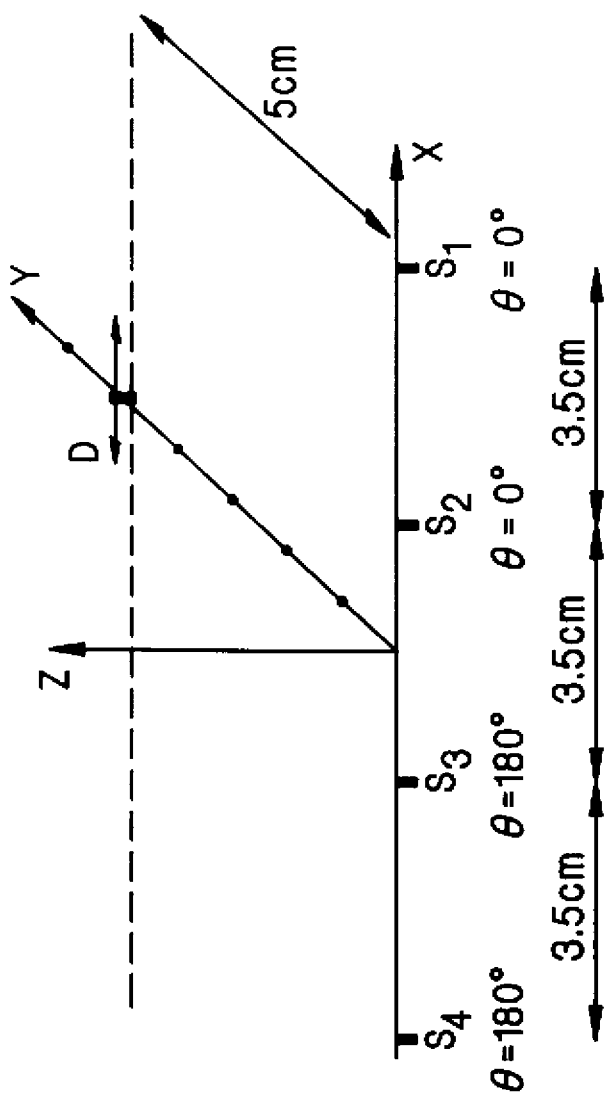
FIG. 8A depicts an experimental arrangement of sources of a four element phased array and a detector.
Figure 8B:
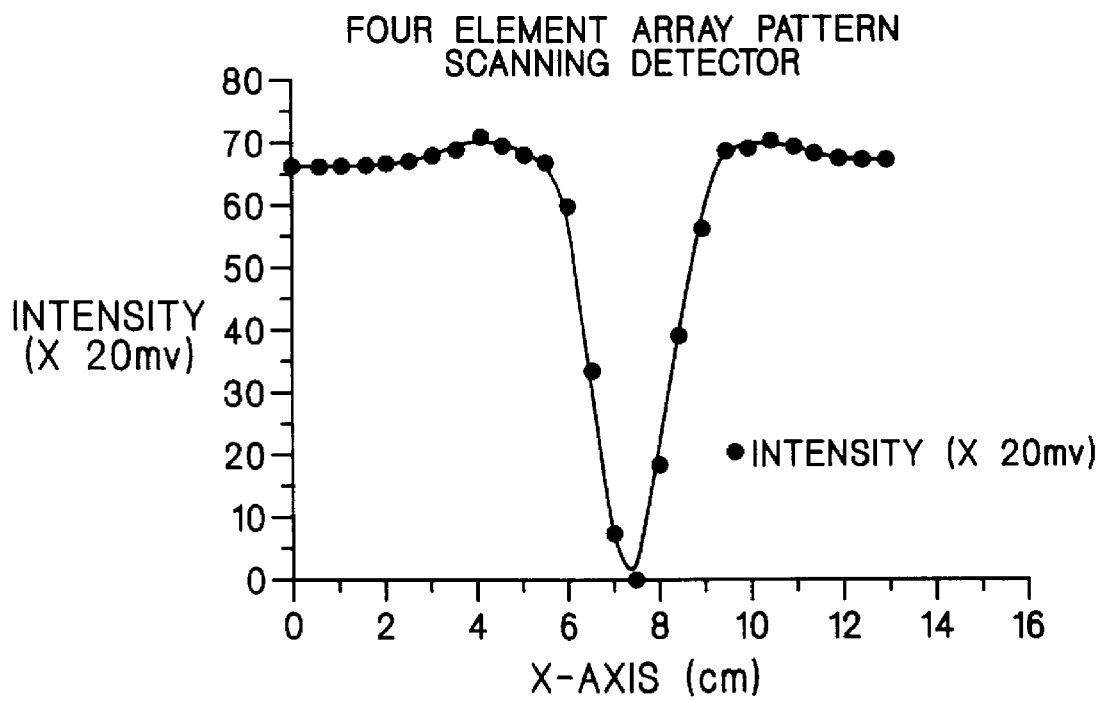
FIGS. 8B and 8C display the intensities and the phase shifts measured for the four element array of FIG. 8A, respectively.
Figure 8C:
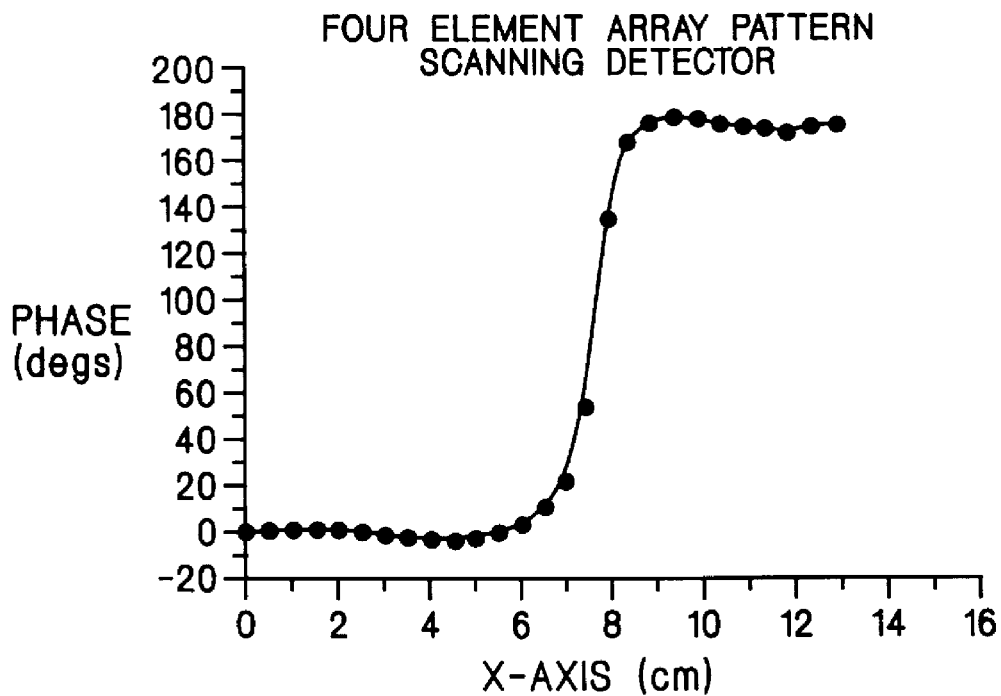

In the preferred mode of operation, the array of sources is phased 180° apart, as shown in FIG. 8A. There is a sharp 180° transition of photon density wave, a large gradient in photon density, from $S_2$, $S_2$ sources to the $S_3$, $S_4$ sources. Thus, the radiated field gives an amplitude null and a phase transition of 180° corresponding to the y-z plane, i.e., perpendicular to the detector. If a larger number of similarly phased sources is used, the transitions are even sharper. The array produces a uniform photon density pattern on each side of the array, as shown in FIGS. 8B and 8C. If an absorbing object is placed in this directional field of diffusing optical waves, imbalance in the photon density is measured. The detection of a hidden object is accomplished by translating the experimental transmitter-receiver system of FIG. 8A.

In addition to the mechanical scanning achieved by moving of the input-output port system, electronic scanning can be performed using the multiple source and multiple detector system of FIG. 2. As shown in FIG. 2B for an array of five sources, there is a 180° phase transition in the resulting migrating field due to the 180° phase difference between the antiphased sources radiating amplitude modulated light. The plane of the 180° phase transition can be shifted in parallel by appropriately varying the apportionment of 0° and 180° phases on the sources. This is performed by sequentially switching the phase of the sources by 180°. In each case, the detection port located on this plane is used for collecting the data. As the sources are electronically switched by 180°, the detection array can be also electronically switched from one detection port to another. The signal from the receiving optical fiber is coupled to one shared PMT detector. However, the system can also include several detectors. If the systems of FIGS. 1 or 1A are used, the electronic source scanning can be combined with synchronous mechanical movement of the detection port.

In general, the invention utilizes the photon density gradient created in the migrating field since it increases the resolution of the detection. As known to one skilled in the art, the photon density gradient formed by interference effects of introduced waves can be created not only by appropriate phasing of the sources but also by other methods such as appropriately spacing the sources, creating an imbalance in the radiated intensity of the individual sources, and other. The imbalance may be achieved by modulating the amplitude of one source with respect to another; this displaces the null in the corresponding direction. Furthermore, the introduced signal can be encoded by the frequency or a selected phase.

FIG. 8A shows the arrangement of the input ports 11 to 17 and detection port 19 of FIG. 1. As described above, light of each laser diode 12 through 18 is intensity modulated at the 200 MHz frequency. Wavelength of the intensity modulated radiation is $$\lambda = \left(\frac{4\pi c/n}{3f\mu_s}\right)^{1/2}$$

wherein f is the modulation frequency of 200 MHz, $\mu_s$ is the scattering factor which is approximately 10 cm$^{-1}$ in an Intralipid solution with refractive index n, and c is $3\times10^8$ cm/s. Thus, the expected wavelength is about 7 cm. The input ports $S_1$, $S_2$, $S_3$, and $S_4$ are set 3.5 cm apart and are anti-phased by 180° using a push pull transformer. The antiphased array creates a large gradient in photon density chosen to take advantage of the destructive interference with the null detection. The laser diodes emitting 754 nm light are intensity modulated at 200 MHz using master oscillator 22, and the local oscillator 26 is operating at 200.025 MHz to perform the dynode modulation of PMT detector 24. The detected intensities and phase shifts of an x-direction scan (FIG. 8A) of detection port 19 are plotted in FIGS. 8B and 8C, respectively. As expected, the intensity has a sharp minimum in between sources $S_2$ and $S_3$ where the phase is changed 180°. The peak width at half maximum is about 2 cm. In addition to the x-direction scan of the detection port, the detection port was scanned in y-direction wherein, as expected, no variation was observed.

Figure 9A:
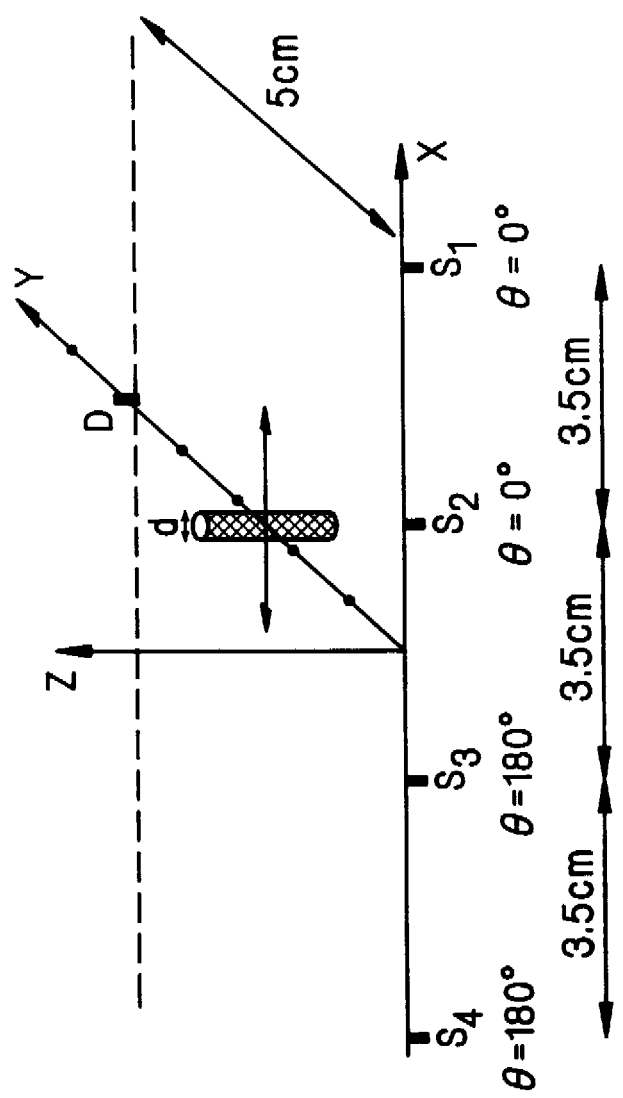
FIG. 9A depicts an experimental arrangement of sources of a four element phased array, a detector, and a strongly absorbing object.
Figure 9B:
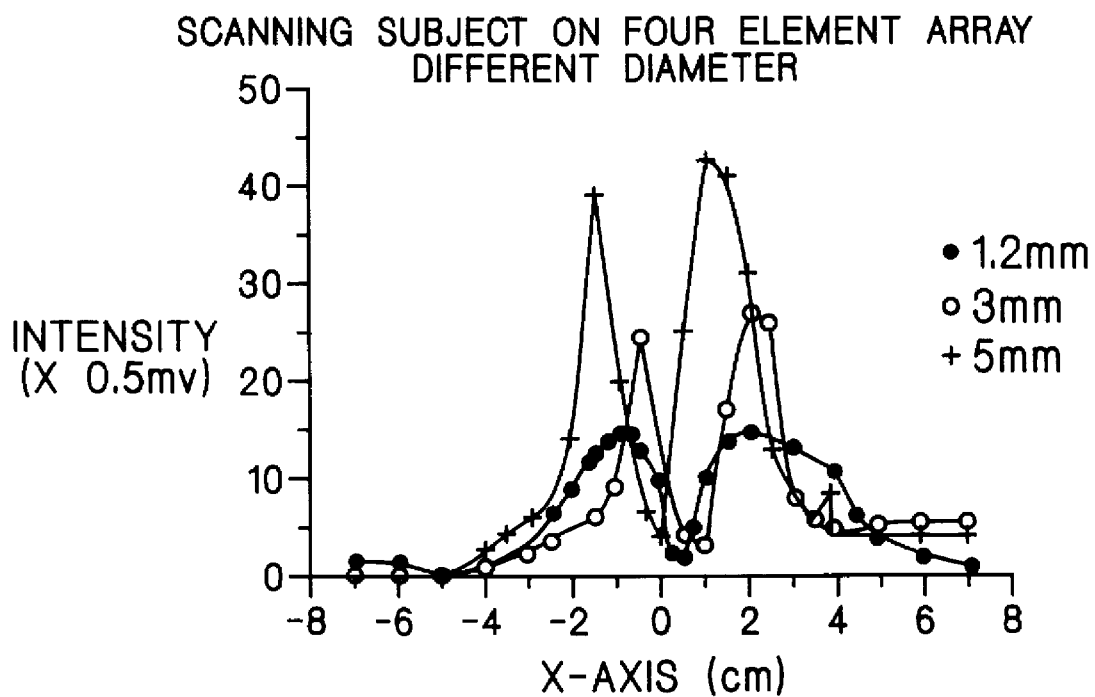
FIGS. 9B, 9C display respectively the intensities and the phase shifts measured for the four element array of FIG. 9A scanning absorbing objects of different sizes.
Figure 9C:
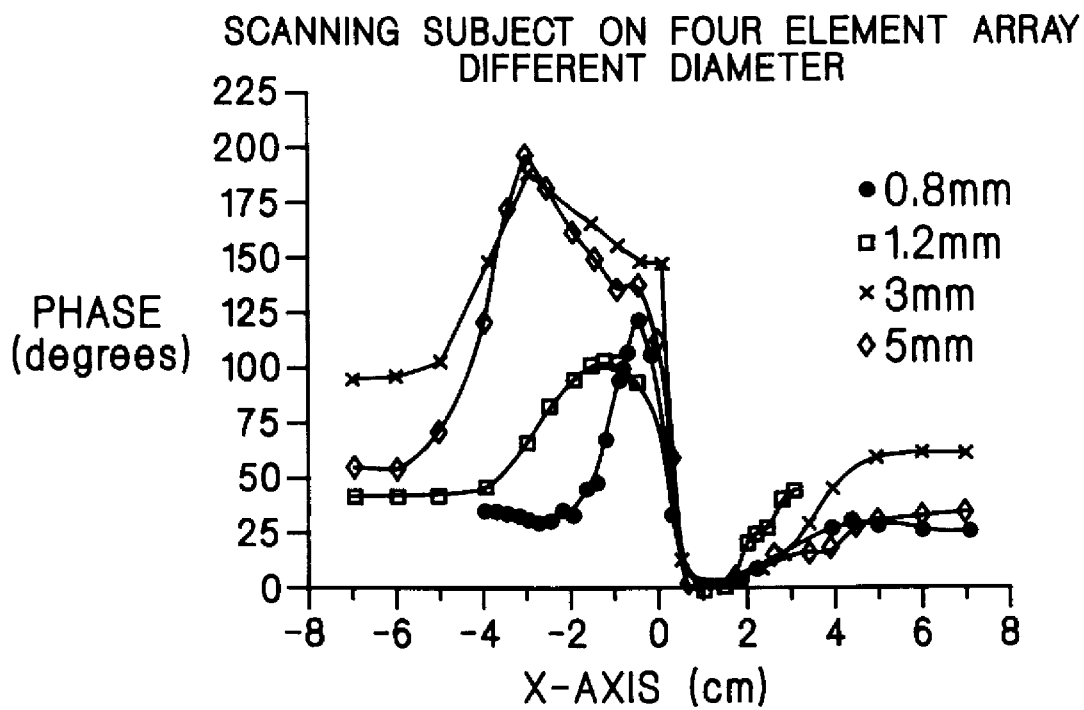

Referring to FIG. 9A, cylindrical objects of different diameter, d, were scanned using the previously described phased array. The objects were placed in the middle of the linear array displaced 2.5 cm from the x-axis. The detection port was located on the x-axis and each object was moved parallel to the x-axis at the 2.5 cm y displacement. The intensity and phase shift detected at different locations are plotted in FIGS. 9B and 9C, respectively. The intensity pattern for each moving object has two maximum and one minimum when the scanned object was located at x=0, y=2.5 point during its scan along the x-axis. At this point, a large phase change is detected, as shown in FIG. 9C. The phase detection has inherently larger resolution of a localized absorber; a hidden object of size as small as 0.8 mm can be detected.

Figure 9D:
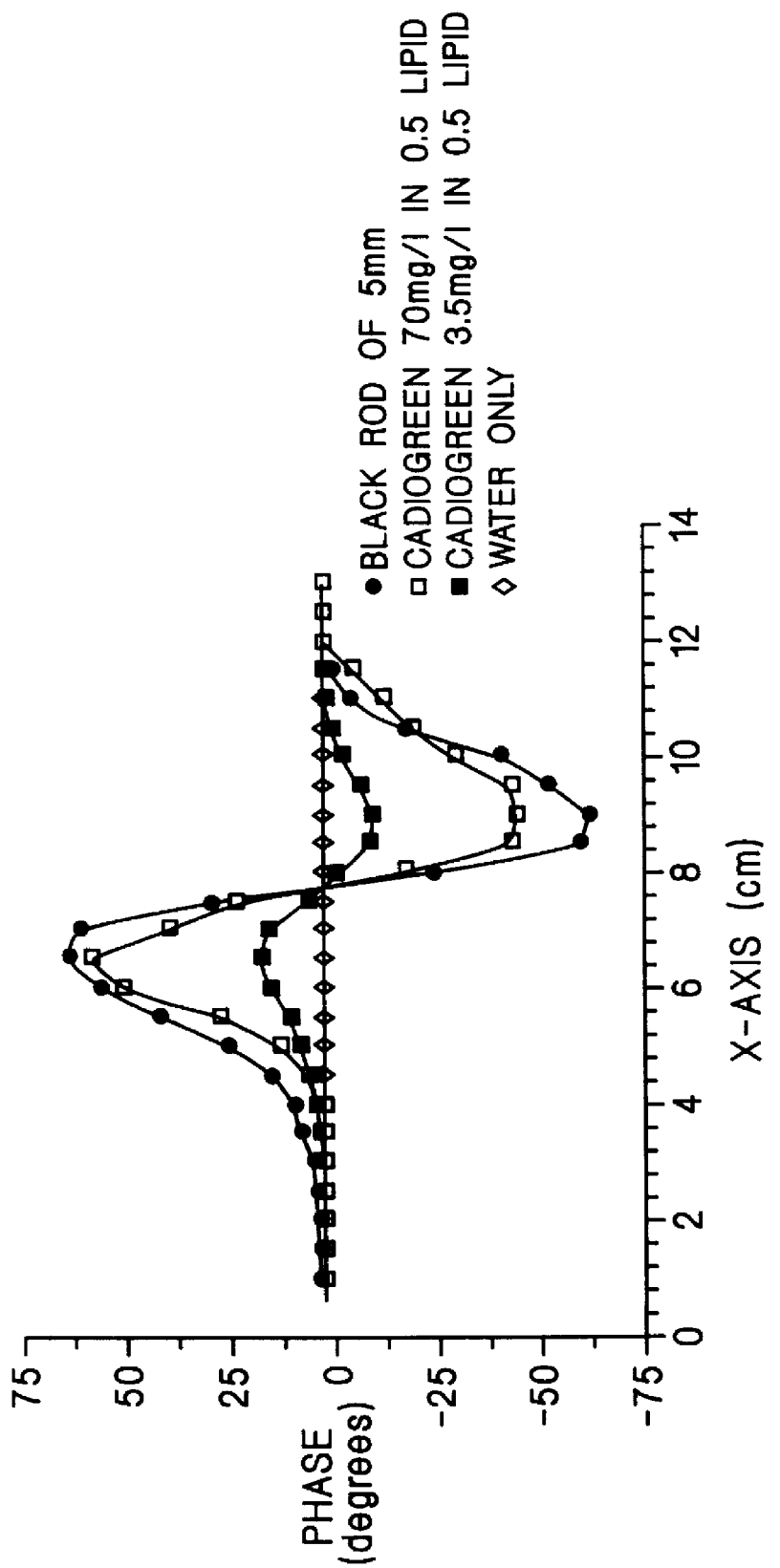
FIG. 9D displays the phase shifts measured for the four element array of FIG. 9A scanning absorbing objects of different absorption coefficients.

The response due to different absorption of the hidden object was studied using a 5 mm cylinder of different absorption coefficient scanned by the 4 element phased array of FIG. 9A. The detected phase change is shown in FIG. 9D. The 5 mm black rod displays the largest phase change due to its high absorption, and the cylinder filled with cardiogreen 3.5 mg/l which has absorption coefficient $\mu_a$=200 cm$^{-1}$ shows the smallest phase change. In scanning of a hidden object, these experiments correspond to mechanically displacing the source detector system, or electronically scanning the subject.

Figure 10A:
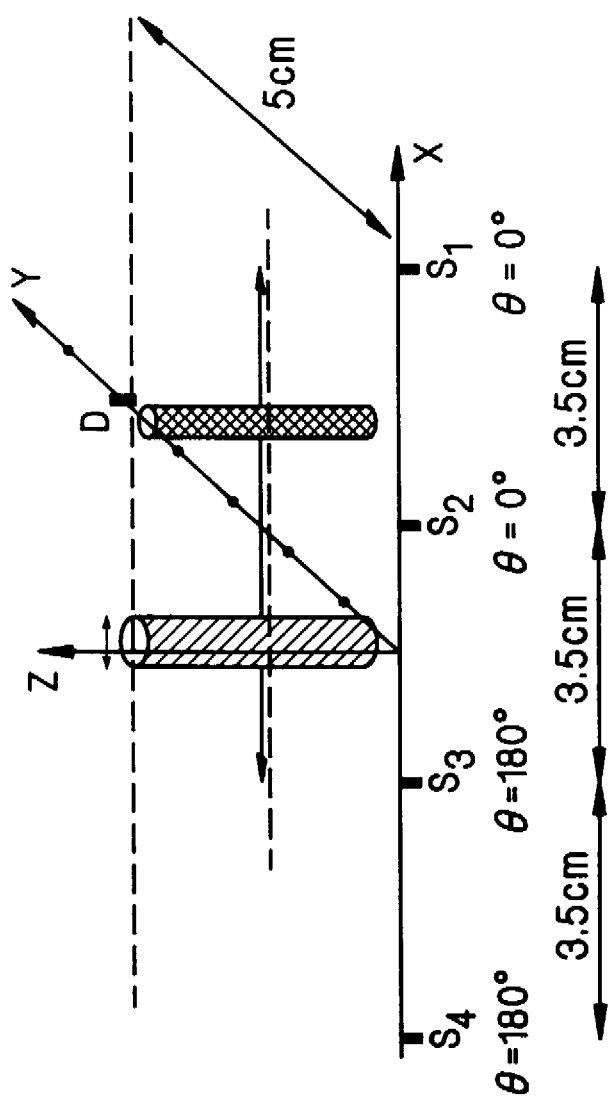
FIG. 10A an experimental arrangement of sources of a four element phased array, a detector, and two strongly absorbing objects.
Figure 10B:
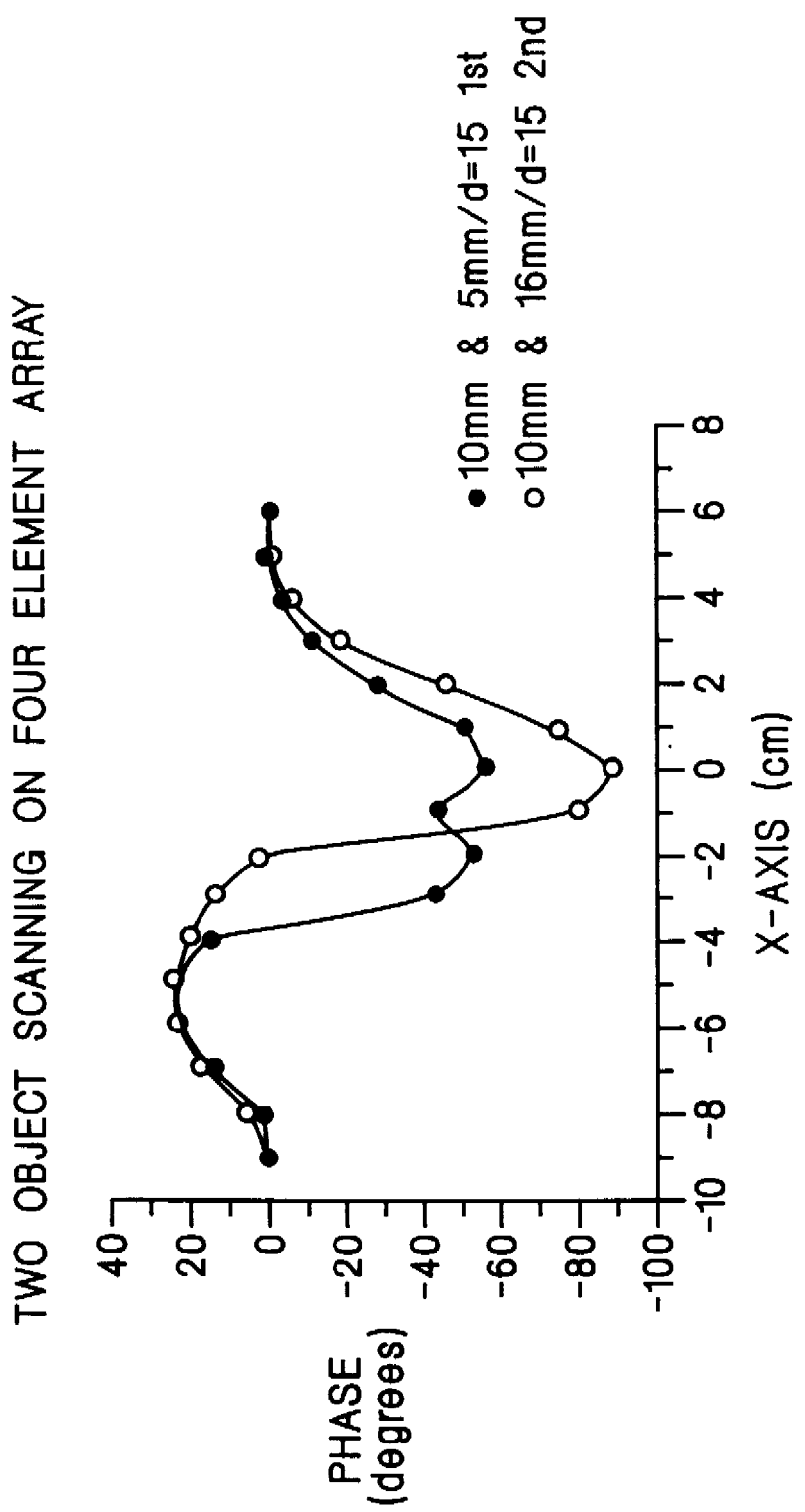
FIG. 10B displays the phase shifts measured for the four element array of FIG. 10A scanning two absorbing objects of different sizes.

Scanning of two objects of a different diameter is shown in FIG. 10A. Two cylinders of different diameter are scanned across the four element phased array located on the x-axis. The detection port is located at y=5 cm. In FIG. 10B the detected phase change is plotted against the displacement of these objects. Curve A represents the phase change of two cylinders of diameters 5 mm and 10 mm separated 3 cm apart. Curve B was measured using 16 mm cylinder instead of the 5 mm cylinder. In this case, wherein the two cylinder separation is smaller, the phase detector can not resolve the two objects.

The imaging resolution is increased by increasing the number of elements of the phased array, since the main lobe of the resultant beam becomes much sharper, the gradient of photon density is larger. Phased arrays of different number of elements and different shapes are used for imaging different organs. For example, in tumor imaging, the four element phased array of FIG. 8A having an approximately linear shape can be used for imaging of the brain. On the other hand, a rectangular or a circular phased array would be used for imaging of a hidden tumor in the breast. The modulation frequency and the element spacing is adjusted to obtain proper focussing in each case.

In general, an imaging system will operate using the following modes of operation that arise from the above-described principles. In the first mode of operation, a series of zero phased, appropriately spaced sources create photon diffusion waves. One or more detectors sensitive to a selected wavelength detect the phase and the amplitude of the migrating wave. Individual sources and detectors may be coded and activated according to selected detection and display schemes. The second mode of operation uses a series of sources phased at 0° and 180° (or any other offset phase that gives adequate sensitivity) with respect to each other. The detector set at the null point of the array detects changes in the phase at the null point. Each detector may use an interference filter to limit its sensitivity to a selected wavelength. The third mode of operation may further complement the second mode by not only detecting the phase transition but also the amplitude null. The most sensitive detection is achieved when a hidden object is located in the midline plane of the 0°–180° signal. An object is located using both signals and their appropriate integrals or derivatives are used to enhance the resolution of the system. The display will also utilize information from several wavelengths, for example, when 750 nm and 850 nm sources are used, the signal difference provides information about the hemoglobin oxygenation and the sum about the blood concentration. Other wavelengths sensitive to endogenous or exogenous tissue pigments may be used. The same source array may be designed to operate in all three modes of operation. A computer supervisory system selects a suitable mode of operation for optimal sensitivity.

Figure 11:
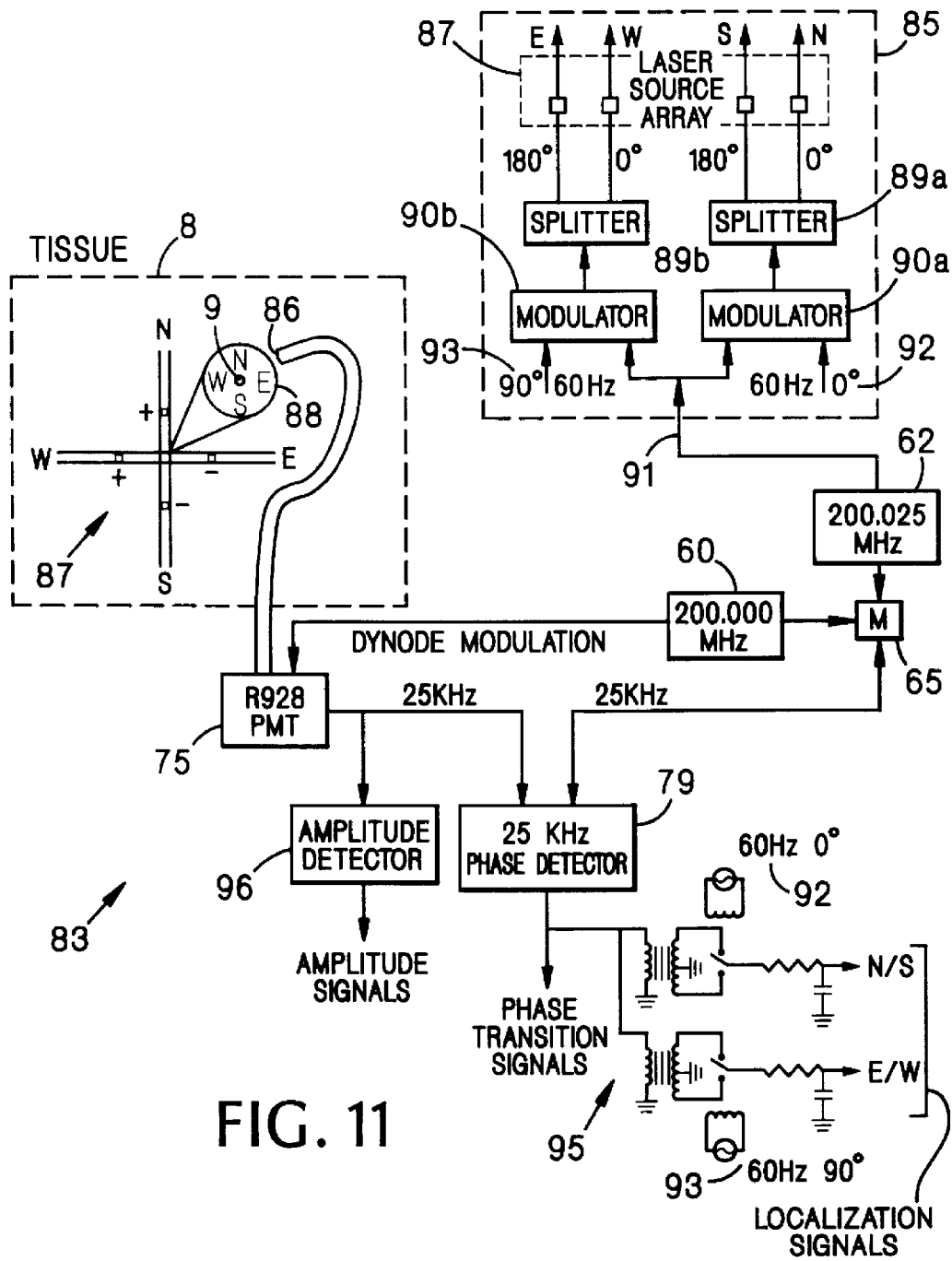
FIG. 11 depict diagrammatically a single wavelength localization system utilizing a conical scanner.

Referring to FIG. 11, a single wavelength localization system 83 employs a conical scanner 85 that introduces optical radiation of a selected wavelength from four laser sources 87 to tissue 8. The relationship of the introduced patters is selected so that the resulting introduced radiation pattern forms a cone scanning in the examination space. The operation principles of array 87 were described in connection with FIGS. 2A, 2B and 2C. Oscillator 62 generates a 200.025 MHz drive signal 91 that is introduced to modulators 90a and 90b. Furthermore, the phase of the drive signal is shifted by 90° in modulator 90a relative to the phase of the drive signal is modulator 90b, and the phase signals are varied over time at 60 Hz. Each of the quadrature phase signals (92, 93) are splitted in splitter 89a and 89b to from an in-phase and anti-phase drive signals. The four drive signals drive four laser diodes labeled N, S, W and E of array 87. Thus array 87 generates a scanning conical signal (88) that includes a sharp phase change in the center of the signal cone. Array 87 has four 780 nm laser diodes, but other wavelengths selected for a high sensitivity to a tissue component may be employed. Furthermore a multi-wavelength array can also be used.

The introduced diffusive photon density wave migrates in tissue 8 and is detected at optical port 86 of an optical fiber connected to PMT detector 75. As described above, the detected radiation is heterodyned using a 200 MHz reference signal and the corresponding 25 kHz signal is coupled to amplitude detector 96 and phase detector 79. Phase detector 79 measures the phase shift between the introduced and detected radiation patterns. The output of the phase detector is correlated with the 60 Hz signals 92 and 93 to produce localization signals corresponding to the N, S, W and E laser sources. The localization signals may be monitored using an oscilloscope.

When port 86 is symmetrically arranged in respect to the location of the radiation cone 88 and there is no field perturbation (i.e., no hidden object 9), the oscilloscope will display a circular pattern. In the same arrangement of cone 88 and port 86, if hidden object 9 is located in the radiation field, the oscilloscope pattern will no longer be symmetrical, e.g., the circular pattern may change to an elliptical pattern. For maximum sensitivity, detection port 86 mechanically scans around tissue 8 and is locked onto the scanning conical signal so that port 86 always points to the center of cone 88, i.e., port 86 is in the null location.

Figure 11A:
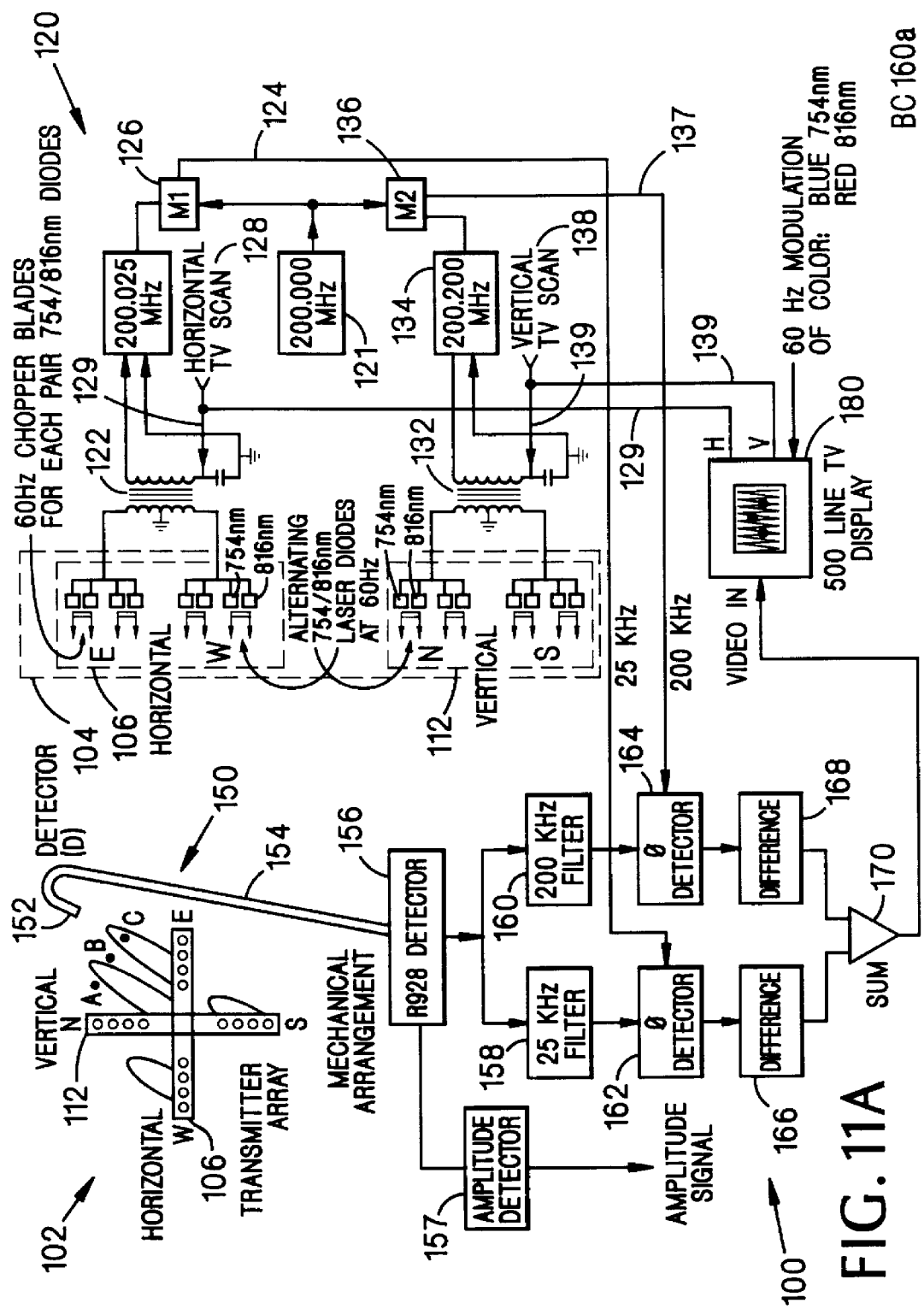
FIGS. 11A and 11B depict diagrammatically imaging systems utilizing one or two dimensional phased array transmitters.

Referring to FIG. 11A, a phase modulation imaging system 100 includes a two-dimensional phased array transmitter 102 connected to laser sources 104. Electronics 120 drives laser sources 104 and also provides reference signals to the detection system. Optical detector 150 includes an optical input port 152 defined by a relatively large area optical fiber 154 connected to a PMT detector 156.

Phased array transmitter 102 includes a horizontal array 106 and a vertical array 112 of input ports connected by a set of optical fibers (not shown in FIG. 11) to laser sources 104 that include 754 nm and 816 nm laser diodes labeled a and b, respectively. Diodes 107, 108, 109, and 110 of the horizontal array 106 are driven by a push-pull transformer 122, and diodes 103, 114, 115, and 116 of the vertical array 112 are driven by a push-pull transformer 124. The resolution of the system may be increased by adding more sources.

The horizontal sources are intensity modulated at a frequency of approximately 200.025 MHz generated by 200.025 MHz oscillator 124 and a horizontal TV scan drive 128 generating a saw-tooth signal of 60 Hz. A horizontal reference signal 127 of 25 kHz supplied to phase detector 162 is produced in a mixer 126 by mixing the 200.025 MHz signal from oscillator 124 and a 200 MHz signal from oscillator 121. The vertical sources are intensity modulated at a frequency of approximately 200.2 MHz generated by a 200.2 MHz oscillator 134 and a vertical TV scan drive 138 generating a saw-tooth signal 139 of 1 kHz. A vertical reference signal 137 of 200 kHz supplied to phase detector 164 is produced in a mixer 136 by mixing the 200.2 MHz signal from oscillator 134 and the 200 MHz from oscillator 121.

The emitted light of either 754 nm or 816 nm, alternated at 60 Hz by a chopper, migrates in the examined tissue as described above and is detected at input port 152. The detected light is heterodyned at PMT detector 156 receiving a reference 200 MHz signal from oscillator 121. The detector signal is then filtered at 25 kHz and 200 kHz using filters 158 and 160, respectively. Phase detectors 162 and 164, receiving 25 kHz and 200 kHz reference signals, respectively, determine at each frequency the phase shift of the detected light in respect to the introduced light.

As described above, the phase shift and the related optical pathlength of the migrating photons directly reflect the tissue properties. System 100 can distinguish the differences in the phase shift of the light emitted from horizontal array 106 and vertical array 112 since the emitted light from each array is modulated at a slightly different frequency.

Transmitter array 102 is designed to reflect the geometry of the examined tissue and a possible location of hidden objects. The hidden objects A, B, and C of FIG. 11 targeted by array 102 are 3 to 4 cm in the scattering medium. Thus, array 102 has the input ports spaced approximately 1 cm apart and equidistantly from the center. Detection port 152 is located about 7 to 10 cm from transmitter 102 and may be mechanically scanned in correlation with the total introduced field of array 102.

PMT detector 156 receives signals from the horizontal and vertical arrays. The modulation offset vertical frequency of the waveform is about 10 times higher than for the horizontal waveform since the repeatability of the vertical scan is higher than the repeatability of the horizontal scan. Approximately the same frequency difference is used for the horizontal and vertical TV scans. The output from phase detectors 162 or 164 represents the phase value as detected along the horizontal axis and the vertical axis. A localized absorbing or scattering object (e.g., a tumor, localized bleeding) will cause a "resonance curve" type response. The detected phase shifts for each signal is differentiated (166 and 168) to "sharpen" the chances and increase the resolution. The horizontal and vertical outputs are added in a summing amplifier 170 and are coupled to a video input of a 500 line TV display 180. The display may be graded in a gray scale or a false color scale. The resolution achieved in the above described one-dimensional experiments can be further improved and the signal-to-noise ratio enhanced by employing a computer storage of the scanned data and integrating over a number of scans and using contrast enhancing algorithms. Alteratively, a "slow scan" TV may be used with narrow banding of the outputs of the phase detectors.

System 100 may also include an amplitude detector 157 that detects the amplitude of the detected radiation at the 25 kHz and 200 kHz frequencies. The detected amplitude signals are manipulated the same way as the phase shift signals and fed to display 180. The use of both the amplitude signals and the phase signals improves resolution of the image.

Figure 11B:
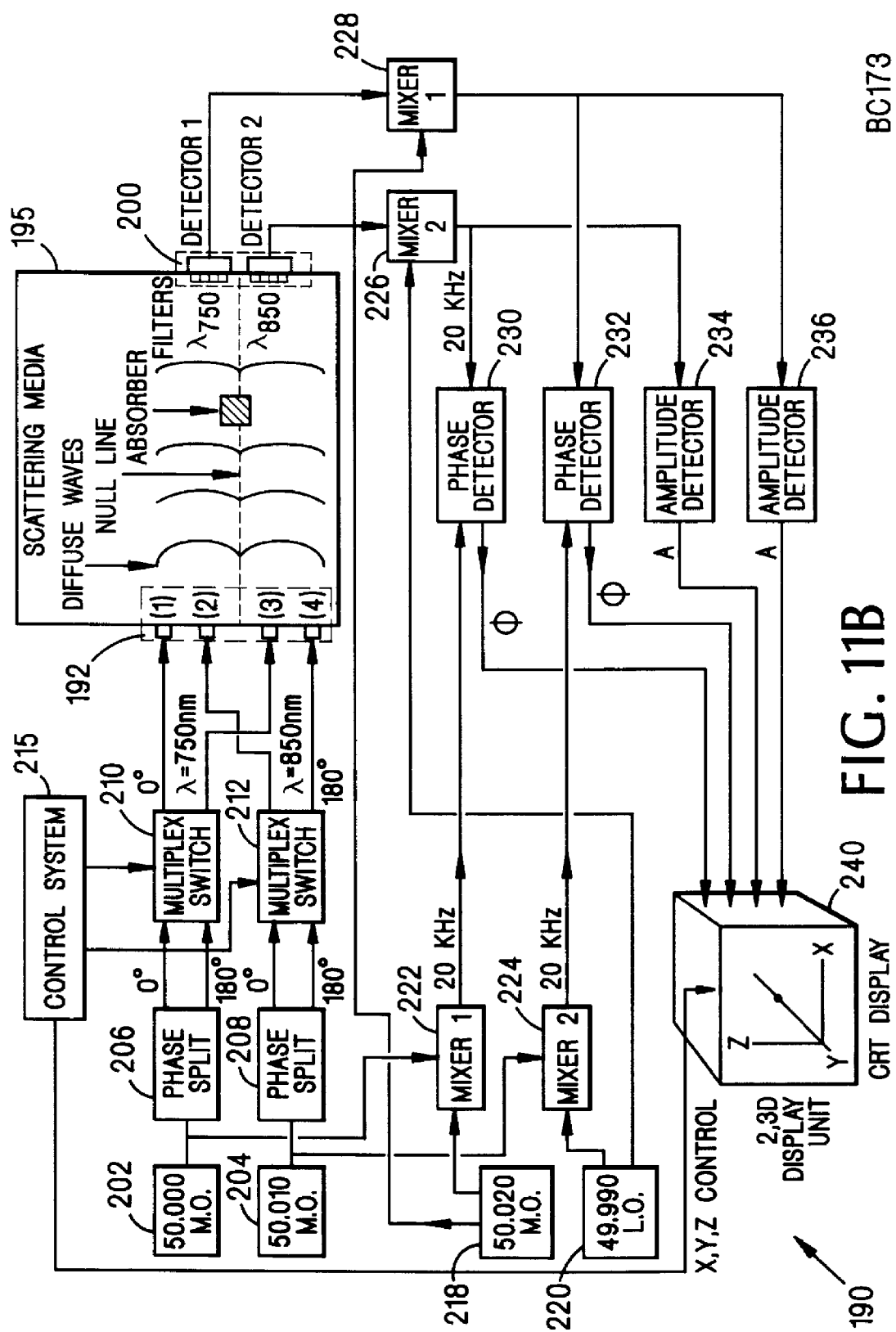

FIG. 11B shows diagrammatically a low frequency imaging system 190 that employs techniques similar to the ones used in system 100 of FIG. 11A. A source array 192 emits diffused waves that propagate in tissue 195 and are detected by detectors 200. The highest resolution is achieved when a hidden object is located on the null line of the diffused waves. The system operates at about 50 MHz, to use instead of the laser diodes LED's and instead of the PMT detectors Si diodes. Oscillators 202 and 204 drive phase splitters 206 and 208, respectively, that provide two intensity modulated voltage signals shifted 180° with respect to each other. The 0° and 180° signals drive 750 nm and 850 nm, LED sources which are multiplexed by switches 210 and 212 to operate sources of one wavelength at the same time. The modulated diffuse waves are detected by the Si diodes that include a wavelength specific interference filter, and the detector signal are converted from 50 MHz and 50.01 MHz frequencies to 20 kHz frequencies using mixers 226 and 228, respectively. Phase detectors 230 and 232 operating at 20 kHz determine the phase shift of the detected signals. Both the phase shift signals and the amplitude signals are used to image the hidden absorber on a display unit 240.

Figure 12A:
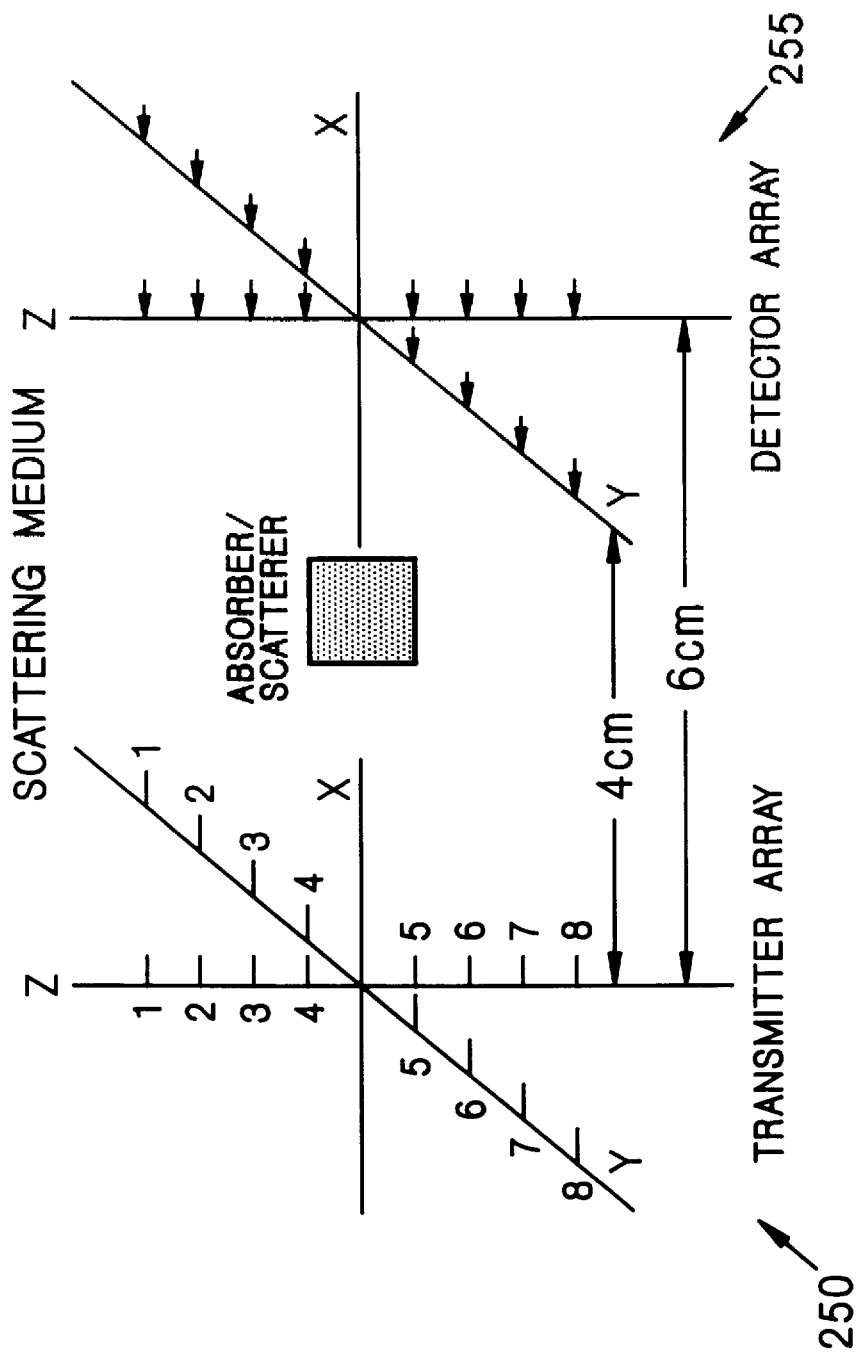
FIGS. 12A and 12B depict an imaging system comprising a two dimensional phased array transmitter and detection array.
Figure 12B:
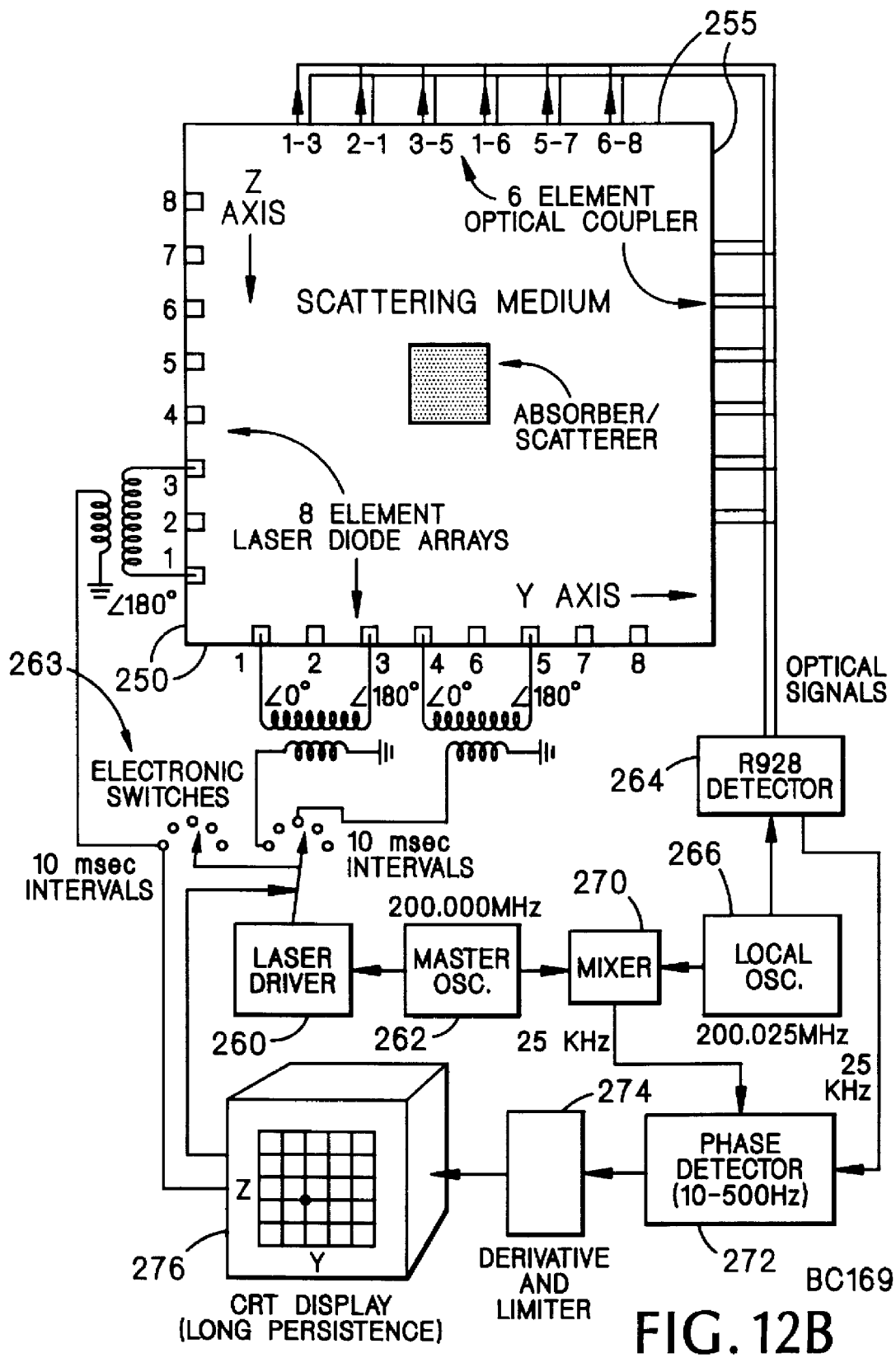

A 2-dimensional transmitter and receiver arrays are shown in FIG. 12A. The spacing of the input ports can be varied depending on the frequency of operation, expected location of the hidden object and the shape of the examined organ. FIG. 12B shows diagrammatically an imaging system utilizing the 2-dimensional transmitter and receiver arrays 250 and 255 that can be switched on electronically. A master oscillator 262 and a laser driver 260 drive a pair of in-phase and anti-phase laser diodes, e.g., the first and the third diode of Y-array and Z-array. A set of electronic switches is used to connect a different set of laser diodes every 10 msec. A set of optical fibers transmits the detected light to a PMT detector 264 that also receives a reference 200.025 MHz signal from a local oscillator 266.

The heterodyned resulting signal is sent to a phase detector 272 that measures the phase shift of the detected radiation. The measured phase shift is further manipulated to enhance the detected changes on a CRT display 276 which has the same 10 msec time base as electronic switches 263. Differenciator 274 takes a derivative of the phase shift signal; this intensifies the crossover of the phase shift shown in FIGS. 8c, 9c and 9d.

Alternative Embodiments

In addition to the above described directional detection, the present invention envisions imaging systems constructed to calculate the average migration pathlengths. Referring to FIG. 4, in such system the drive signal from oscillator 60 is introduced to a selected laser diode 64a, . . . , 64n or 66a, . . . , 66n using switches 61a, . . . , 61n. The intensity modulated radiation of each laser diode is coupled to tissue 70 at an input port located at a precisely defined position. A detection port located at another position detects radiation that has migrated in tissue 70. The detected signal is heterodyne mixed directly at PMT detector 74. These signals are fed into the phase detector wherein the phase and the intensity of the detected radiation are measured. The system may include several PMT detectors and phase detectors (only one set of detectors is shown in FIG. 4) operating simultaneously or one detector scans the surface of tissue 70. The phase shift and the intensity of the detected heterodyned signal depend on the tissue through which said scattered and absorbed radiation migrated.

The tissue properties are determined from the detected phase shift and intensity values and from the known input ports and detection port geometries. The measured average pathlengths, <L>, can also be determined. The detected phase shift is converted to an effective migration pathlength <L> by using the low frequency approximation $\theta = 2\pi f <L> n/c$, wherein f is the modulation frequency, c is the speed of light ($3 \times 10^8$ cm/s), and n is the refractive index of the medium.

Figure 5A:
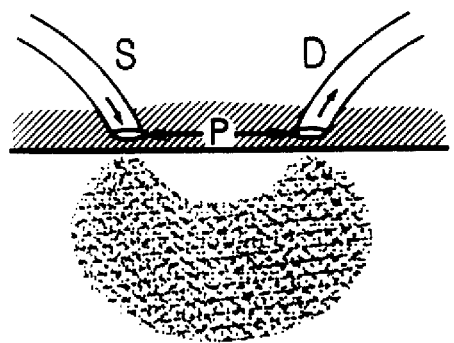
FIGS. 5A, 5B, and 5C illustrate changes in optical field propagating in a strongly scattering medium which includes a strongly absorbing component.
Figure 5B:
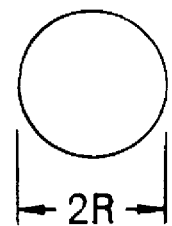
Figure 5B:
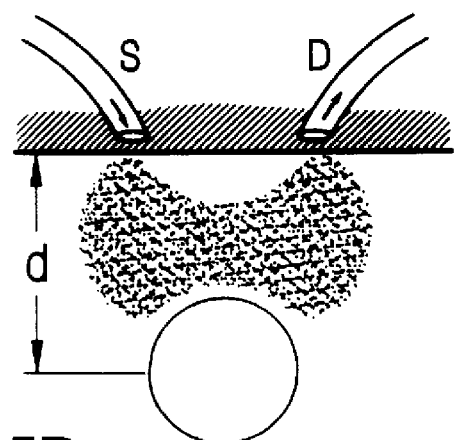
Figure 5C:
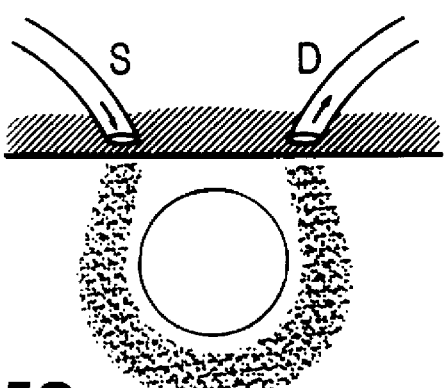

To illustrate imaging by detecting migration pathlengths, we use an example of photon migration in a tissue with a strongly absorbing object, a perfect absorber($\mu_a \rightarrow \infty$) of radius R. Referring to FIGS. 5A, 5B, and 5C the distribution of pathlengths defines an optical field that exists between a point detector, D, and source, S, separated by distance $\rho$ and located on the exterior of an examined tissue which is a semi-infinite, strongly scattering medium. As shown in FIG. 5A, infinitely far away from the field, a perfect absorber does not alter the banana-shaped optical field of photons emitted by source S and detected at detector D. As the object enters the optical field (FIG. 5B), the photons which have migrated the farthest distance from D and S are eliminated by the absorption process inside the perfect absorber of radius R. Since photons which travel the longest pathlengths are absorbed, the approach of an object shortens the distribution of pathlengths, or alternatively, shortens the average pathlength <L>. As the object moves closer, and the optical field surrounds the object (FIG. 5C), some of the detected photons have travelled "around" the object, which is detected as lengthening the distribution of pathlengths. Thus, the average pathlength measurement can reveal location of a strongly absorbing component of a tissue (e.g., tumor or localized bleeding).

Even though this pathlength computation approach requires in most cases extensive computational capabilities, it can yield useful information in the localization procedures and can provide a useful supplement to the above described directional approach.

What is claimed is:

1. A spectroscopic system for examination of biological tissue comprising:

at least one light source, operatively connected to at least one oscillator, constructed to generate optical radiation of a visible or infrared wavelength, said radiation being intensity modulated at a selected frequency of said oscillator to achieve a known radiation pattern, multiple input ports, placed at selected locations relative to the examined tissue, optically connected to said at least one light source and constructed to introduce simultaneously optical radiation to the examined tissue at the corresponding tissue locations, a radiation pattern controller constructed to control the radiation intensity or phase relationship of patterns simultaneously introduced from said multiple input ports, said introduced patterns forming resulting radiation that possesses a substantial gradient of photon density in at least one direction, said resulting radiation being scattered and absorbed in migration paths in the examined tissue, a detection port placed at a selected location relative to the examined tissue, an optical detector, optically connected to said detection port, constructed and arranged to detect over time the resulting radiation that has migrated in the tissue to said detection port, a processor, operatively connected to and receiving signal from said detector, arranged to process signals of said detected radiation in relation to said introduced radiation to create processed data indicative of influence of the examined tissue upon said substantial gradient of photon density of said resulting radiation, and an imager, including a display, connected to and receiving said processed data from said processor, said imager being constructed to produce image data representing the influence of the examined tissue upon said substantial gradient of photon density over a multiplicity of detection locations and to display said image data on said display.

2. The system of claim 1 wherein said multiple input ports are arranged to form a one dimensional array shaped to examine a selected organ of a human body.

3. The system of claim 1 wherein said multiple input ports are arranged to form a two dimensional array is shaped to examine a selected organ of a human body.

4. The system of claim 2 or 3 wherein said shape fits a head or a female breast.

5. The system of claim 1 wherein said wavelength is sensitive to a wavelength sensitive agent present in the examined tissue and said processed data also indicate of the influence of said wavelength sensitive agent upon said steep phase change or said sharp minimum in the intensity of said radiation.

6. The system of claim 1 further comprising a phase detector, connected to and receiving signals from said optical detector, constructed to detect the phase of the detected radiation, said phase being utilized by said imager.

7. The system of claim 1 further comprising an amplitude detector, connected to and receiving signals from said optical detector, constructed to detect the amplitude of the detected radiation, said amplitude being utilized by said imager.

8. The system of claim 1 further comprising a second light source, optically connected to said input ports, constructed to generate radiation of a second selected wavelength in the visible or infrared range.

9. The system of claim 1 further comprising:
a second detection port placed at a selected location relative to the examined tissue,
an second optical detector, optically connected to said second detection port, constructed and arranged to detect over time the resulting radiation that has migrated in the tissue to said detection port, and
said processor, receiving signal from said first detector and said second detector, further arranged to process signals of said first detector and said second detector in a relative phase shifted relationship to create said processed data.

10. The system of claim 9 wherein said relative phase shifted relationship comprises a 180 degree phase shift between said first detector signal and said second detector signal.

11. A spectroscopic system for examination of biological tissue comprising:
at least one light source, operatively connected to at least one oscillator, constructed to generate optical radiation of a visible or infrared wavelength, said radiation being intensity modulated at a selected frequency of said oscillator to achieve a known radiation pattern,
multiple input ports, placed at selected locations relative to the examined tissue, optically connected to said at least one light source and constructed to introduce simultaneously optical radiation to the examined tissue at the corresponding tissue locations,
a radiation pattern controller constructed to control the radiation intensity or phase relationship of patterns simultaneously introduced from said multiple input ports, said introduced patterns forming resulting radiation that possesses a substantial gradient of photon density in at least one direction, said resulting radiation being scattered and absorbed in migration paths in the examined tissue,
a detection port placed at a selected location relative to the examined tissue,
an optical detector, optically connected to said detection port, constructed and arranged to detect over time the resulting radiation that has migrated in the tissue to said detection port,
a processor, operatively connected to and receiving signal from said detector, arranged to process signals of said detected radiation in relation to said introduced radiation to create localization signals indicative of influence of the examined tissue upon said substantial gradient of photon density of said radiation, and
an imager, including a display, connected to and receiving said localization signals from said processor and being constructed to display said localization signals indicating scattering or absorption of the examined tissue over a multiplicity of detection locations.

12. The system of claim 11 wherein said processor further comprises a phase detector constructed to detect the phase of the detected radiation.

13. The system of claim 11 wherein said processor further comprises an amplitude detector constructed to detect the amplitude of the detected radiation.

14. The system of claim 1, or 11 wherein said phase relationship of radiation patterns introduced from two adjacent input ports of said multiple input ports is 180 degrees.

15. The system of claim 11 further comprising a second light source, optically connected to said input ports, constructed to generate radiation of a second selected wavelength in the visible or infrared range.

16. The system of claim 15 further constructed to introduce said radiation of said wavelengths in a time-shared manner.

17. The system of claim 11 wherein said multiple input ports are arranged to form a one dimensional array shaped to examine a selected tissue region of a human body.

18. The system of claim 11 wherein said multiple input ports are arranged to form a two dimensional array is shaped to examine a selected tissue region of a human body.

19. The system of claim 17 or 18 wherein said shape fits a head or a female breast.

20. The system of claim 1 or 11 further comprising multiple detection ports optically connected to at least one said detector and placed at selected locations relative to the examined tissue, said detection ports forming a one dimensional array or a two dimensional array.

21. The system of claim 1 or 11 wherein said processor further calculates from said processed data an absorption coefficient $\mu_a$ or a scattering coefficient $\mu_s$.

22. The system of claim 11 wherein said resulting radiation forms a cone scanning in the examined tissue and said localization signals include a non-symmetrical pattern indicating presence of an abnormal tissue region of different scattering or absorption properties.

23. The system of claim 1 or 11 wherein said input and detection ports are arranged in a transmission geometry.

24. The system of claim 1 or 11 wherein said wavelength is sensitive to a wavelength sensitive agent present in the examined tissue and said processed data also indicate of the influence of said wavelength sensitive agent upon said steep phase change or said sharp minimum in the intensity of said radiation.

25. The system of claim 11 wherein said imager further employs a contrast enhancing algorithm on said localization signals.

26. The system of claim 11 wherein said imager further employs a contrast enhancing algorithm that includes differentiation of the localization signals.

27. The system of claim 11 wherein said imager further employs a contrast enhancing algorithm that includes integration of the localization signals.

28. The system of claim 1 or 11 wherein said radiation pattern controller is constructed to alter the relative phase, the relative amplitude or the relative frequency of said introduced radiation patterns to achieve electronic scanning of said gradient of photon density of said resulting radiation over the examined tissue.

29. The system of claim 1 or 11 further comprising a mechanical scanning device constructed to move said input ports to different locations on a predetermined geometric pattern relative to the examined tissue.

30. The system of claim 1 or 11 further comprising a mechanical scanning device constructed to move said detection port to a different location on a predetermined geometric pattern relative to the examined tissue.

31. The system of claim 1 or 11 wherein said oscillator operates at a frequency in the range of 40 MHz to 1 GHz.

32. The system of claim 1 or 11 wherein said oscillator operates at a frequency of about 50 MHz.

33. The system of claim 32 wherein said light source is a LED diode and said detector is a diode detector.

34. The system of claim 1 or 11 wherein said oscillator operates at a frequency of about 200 MHz.

35. The system of claim 34 wherein said light source is a laser diode and said detector is a PMT.

36. The system of claim 1 or 11 wherein said substantial gradient of photon density includes a steep phase change or a sharp minimum in the intensity of said resulting radiation.

37. The system of claim 1 or 11 wherein said wavelength of said light source is 754 nm, 760 nm, 780 nm, 800 nm, 816 nm, 840 nm or 850 nm.

38. The system of claim 1 or 11 wherein said oscillator is an element of a double side band modulator constructed to produce said intensity modulation.

39. The system of claim 1 or 11 wherein said detector is a photomultiplier constructed for heterodyne detection.

40. A spectroscopic method of examination of biological tissue of a subject, comprising the steps:
providing at least one light source of electromagnetic radiation of a visible or infrared wavelength, said radiation being intensity modulated at a selected frequency, said source being optically connected to multiple input ports, and further providing a detection port optically connected to an optical detector;
introducing simultaneously into the examined tissue, at said input ports, said intensity modulated radiation having a known time-varying pattern of photon density, a time relationship, radiation intensity or phase of said patterns being selected by a pattern controller to form resulting introduced radiation that possesses, in at least one direction, a substantial gradient in photon density as a result of interaction of the simultaneously introduced patterns emanating from said input ports, said resulting radiation being scattered and absorbed in migration paths in the examined tissue;
detecting over time, at a detection port placed at a selected location on the examined tissue, said radiation that has migrated in the examined tissue;
processing signals of said detected radiation in relation to said introduced radiation to create processed data indicative of influence of said examined tissue upon said substantial gradient of photon density; and
imaging the examined tissue by displaying image data representing the influence of the examined tissue upon said substantial gradient of photon density over a multiplicity of detection locations.

41. The method of claim 40 further comprising the steps of
moving synchronously said input ports or said detection port to different locations on a predetermined geometric pattern relative to the examined tissue;
introducing into the examined tissue, at each said input port, said radiation;
detecting over time, at said detection port said radiation that has migrated in the examined tissue;
processing signals of said detected radiation in relation to said introduced radiation to create processed data indicative of the influence of said examined tissue upon said gradient of photon density; and
imaging the examined tissue of said different location by displaying image data created from said processed data received from said processor.

42. The method of claim 40 further comprising the steps of
introducing said radiation while electronically scanning said gradient of photon density of said resulting radiation over the examined tissue;
detecting over time, at said detection port said radiation that has migrated in the examined tissue;
processing signals of said detected radiation in relation to said introduced radiation to create processed data indicative of the influence of said examined tissue upon said gradient of photon density; and
imaging the examined tissue of said different location by displaying image data created from said processed data received from said processor.

43. The method of claim 42 wherein said electronic scanning step is performed by varying the relative phase, the relative amplitude or the relative frequency of said introduced radiation patterns.

44. The method of claim 40, 41 or 42 further comprising the step of positioning said detection port in the direction of said gradient of photon density.

45. The method of claim 40, 41 or 42 further comprising the step of detecting the phase of said detected radiation and utilizing said phase in said imaging.

46. The method of claim 40, 41 or 42 further comprising the step of detecting the amplitude of said detected radiation and utilizing said amplitude in said imaging.

47. The method of claim 40, 41 or 42 further comprising the steps of introducing, at each said input port, said radiation of a second selected wavelength in the visible or infrared range;
detecting over time, at said detection port said radiation of said second selected wavelength that has migrated in the examined tissue;
processing signals of said detected radiation of said second selected wavelength in relation to said introduced radiation of said second selected wavelength to create processed data indicative of the influence of said examined tissue upon said gradient of photon density; and
imaging the examined tissue by displaying image data created from said processed data received from said processor.

48. The method of claim 40 further comprising the steps of:
detecting over time, at multiple detection ports placed at selected locations relative to the examined tissue, said radiation that has migrated in the examined tissue, said detection ports forming a one dimensional array or a two dimensional array;
processing signals of said detected radiation in relation to said introduced radiation to create processed data of multiple detection ports indicative of the influence of the examined tissue upon said gradient of photon density; and
imaging the examined tissue by displaying said image data.

49. The method of claim 40 further comprising the steps of:
detecting over time, at two detection ports placed at selected locations relative to the examined tissue, said radiation that has migrated in the examined tissue,
processing signals detected at said first detection port and said second detection port in a relative phase shifted relationship to create said processed data.

50. The method of claim 49 wherein said relative phase shifted relationship comprises a 180 degree phase shift between the signal detected at said first detection port and the signal detected at said second detection port.

51. A spectroscopic method of examination of biological tissue of a subject, comprising the steps:

providing at least one light source of electromagnetic radiation of a visible or infrared wavelength, said radiation being intensity modulated at a selected frequency, said light source being optically connected to multiple input ports, and further providing a detection port optically connected to an optical detector;

introducing simultaneously into the examined tissue, at each said input port, said intensity modulated radiation of a known time-varying pattern of photon density, a relative time relationship, radiation intensity or phase of said introduced patterns being selected by a pattern controller to form resulting radiation that possesses, in at least one direction, a substantial gradient in photon density as a result of interaction of the simultaneously introduced patterns emanating from said input ports, said resulting radiation being scattered and absorbed in migration paths in the examined tissue;

detecting over time, at a detection port placed at a selected location relative to the examined tissue, said radiation that has migrated in the examined tissue;

processing signals of said detected radiation in relation to said introduced radiation to create localization signals indicative of influence of the examined tissue upon said substantial gradient of photon density; and imaging the examined tissue by displaying said localization signals indicating scattering or absorption of the examined tissue over a multiplicity of detection locations.

52. The method of claim 51 further comprising the steps of moving synchronously said input ports or said detection port to a different location on a predetermined geometric pattern relative to the examined tissue;

introducing into the examined tissue, at each said input port, said radiation;

detecting over time, at said detection port said radiation that has migrated in the examined tissue;

processing signals of said detected radiation in relation to said introduced radiation to create localization signals indicative of the influence of said examined tissue upon said gradient of photon density; and imaging the examined tissue by displaying said localization signals of said location indicating scattering or absorption of the examined tissue.

53. The method of claim 51 further comprising the steps of introducing said radiation while electronically scanning said gradient of photon density of said resulting radiation over the examined tissue;

detecting over time, at said detection port said radiation that has migrated in the examined tissue;

processing signals of said detected radiation in relation to said introduced radiation to create localization signals indicative of the influence of said examined tissue, by said electronic scanning, upon said gradient of photon density; and imaging the examined tissue by displaying said localization signals indicating scattering or absorption of the examined tissue.

54. The method of claim 53 wherein said electronic scanning step is performed by varying the relative phase, the relative amplitude or the relative frequency of said introduced radiation patterns.

55. The method of claim 51, 52 or 53 further comprising locating said detection port in the direction of said gradient of photon density.

56. The method of claim 51, 52 or 53 further comprising the step of detecting the phase of said detected radiation and utilizing said phase in said step of producing said localization signals.

57. The method of claim 51, 52 or 53 further comprising the step of detecting the amplitude of said detected radiation and utilizing said amplitude in said step of producing said localization signals.

58. The method of claim 56 further comprising the step of calculating from said processed data an absorption coefficient $\mu_a$ or a scattering coefficient $\mu_s$.

59. The method of claim 40 or 51 wherein the phase relationship of radiation patterns introduced from two adjacent input ports of said multiple input ports is 180 degrees.

60. The method of claim 40 or 51 wherein said introducing and detecting steps are performed having said input and detection ports arranged in a transmission geometry.

61. The method of claim 60 wherein said imaging step further comprises the step of employing a contrast enhancing algorithm on said localization signals.

62. The method of claim 60 wherein said imaging step further comprises the step of employing a contrast enhancing algorithm that includes differentiation of the localization signals.

63. The method of claim 60 wherein said imaging step further comprises the step of employing a contrast enhancing algorithm that includes integration of the localization signals.

64. The method of claim 40 or 51 further comprising the step of varying frequency of the introduced radiation to alter migration path of said resulting radiation in the examined tissue.

65. The method of claim 40 or 51 wherein said frequency of the introduced radiation is in the range of 40 MHz to 1 GHz.

66. The method of claim 40 or 51 wherein said frequency is about 50 MHz or about 200 MHz.

67. The method of claim 40 or 51 wherein said substantial gradient of photon density includes a steep phase change or a sharp minimum in the intensity of said radiation.

68. The method of claim 40 or 51 wherein said wavelength of said light source is sensitive to a wavelength sensitive agent present in the examined tissue.

69. The method of claim 40 or 51 wherein said wavelength of said light source is 754 nm, 760 nm, 780 nm, 800 nm, 816 nm, 840 nm or 850 nm.

70. The method of claim 40 or 51 wherein said wavelength of said light source is sensitive to an endogenous or an exogenous pigment.

71. The method of claim 40 or 51 wherein said intensity modulation is performed by a double side band modulator.

72. The method of claim 40 or 51 wherein said detector is a photomultiplier and said detecting step includes heterodyne detection.

73. The method of claim 40 or 51 further comprising the steps of introducing radiation of a second wavelength, said radiation being intensity modulated at said frequency and having said known time-varying pattern of photon density.

74. The method of claim 73 wherein said steps of introducing said radiation of said wavelengths is performed in a time-shared manner.

* * * * *

UNITED STATES PATENT AND TRADEMARK OFFICE
CERTIFICATE OF CORRECTION

PATENT NO. : 5,807,263

DATED : September 15, 1998

INVENTOR(S) : Britton Chance

It is certified that error appears in the above-identified patent and that said Letters Patent is hereby corrected as shown below:

This application is an application filed under 35 USC 371 of PCT/US93/05868, international filing date June 17, 1993, which is a continuation-in-part of U.S. Serial No. 900,197, filed June 17, 1992, now U.S. Patent No. 5,353,799.

Under References Cited [56], please insert:

WO 84/04665
WO 92/13598
UK 2,068,537A
EP 099756

Signed and Sealed this

Seventh Day of September, 1999

Attest:

Q. TODD DICKINSON

Attesting Officer

Acting Commissioner of Patents and Trademarks